(12) United States Patent
Friedman et al.

(10) Patent No.: US 7,763,077 B2
(45) Date of Patent: Jul. 27, 2010

(54) REPAIR OF SPINAL ANNULAR DEFECTS AND ANNULO-NUCLEOPLASTY REGENERATION

(75) Inventors: Craig D. Friedman, Westport, CT (US); Arindam Datta, Hillsborough, NJ (US)

(73) Assignee: Biomerix Corporation, New York, NY (US)

( * ) Notice: Subject to any disclaimer, the term of this patent is extended or adjusted under 35 U.S.C. 154(b) by 1687 days.

(21) Appl. No.: 10/746,563

(22) Filed: Dec. 24, 2003

(65) Prior Publication Data

US 2005/0149046 A1 Jul. 7, 2005

(51) Int. Cl.
*A61F 2/44* (2006.01)
*A61B 17/70* (2006.01)

(52) U.S. Cl. ................... 623/17.16; 626/279

(58) Field of Classification Search ... 623/17.11–17.16; 606/279
See application file for complete search history.

(56) References Cited

U.S. PATENT DOCUMENTS

| | | |
|---|---|---|
| 1,896,071 A | 2/1933 | Clark |
| 2,546,754 A | 3/1951 | Jones |
| 2,616,422 A | 11/1952 | Jones |
| 3,175,025 A | 3/1965 | Green et al. |
| 3,279,996 A | 10/1966 | Long |
| 3,334,629 A | 8/1967 | Cohn |
| 3,789,841 A | 2/1974 | Antoshkiw |
| 3,896,819 A | 7/1975 | Zaffaroni |
| 3,946,106 A | 3/1976 | Chien |
| 4,282,199 A | 8/1981 | Lamond et al. |
| 4,315,844 A | 2/1982 | Aboytes |
| 4,459,252 A | 7/1984 | MacGregor |
| 4,503,569 A | 3/1985 | Dotter |
| 4,512,338 A | 4/1985 | Balko et al. |
| 4,531,916 A | 7/1985 | Scantlebury et al. |
| 4,545,390 A | 10/1985 | Leary |
| 4,619,274 A | 10/1986 | Morrison |
| 4,643,184 A | 2/1987 | Mobin-Uddin |
| 4,689,386 A | 8/1987 | Chapman et al. |
| 4,737,152 A | 4/1988 | Alchas |
| 4,739,768 A | 4/1988 | Engelson |

(Continued)

FOREIGN PATENT DOCUMENTS

CA 2385613 12/2005

(Continued)

OTHER PUBLICATIONS

U.S. Appl. No. 60/471,518, filed May 15, 2003, Constantino et al.

(Continued)

*Primary Examiner*—Eduardo C Robert
*Assistant Examiner*—Ellen Rust
(74) *Attorney, Agent, or Firm*—William H. Dippert; Eckert Seamans Cherin & Mellott, LLC

(57) ABSTRACT

The invention relates to the repair of spinal annular defects. An apparatus comprises a scaffold comprised of a biodurable, resiliently compressible, elastomeric reticulated composition to obliterate spinal/vertabral connective tissue defects, to obliterate spinal-annular nuclear tissue defects, and for spinal annulo-nucleoplasty regeneration. The apparatus comprises an at least partially cylindrical member.

24 Claims, 6 Drawing Sheets

U.S. PATENT DOCUMENTS

| | | |
|---|---|---|
| 4,776,337 A | 10/1988 | Palmaz |
| 4,781,177 A | 11/1988 | Lebigot |
| 4,813,934 A | 3/1989 | Engelson et al. |
| 4,832,047 A | 5/1989 | Sepetka et al. |
| 4,832,055 A | 5/1989 | Palestrant |
| 4,871,542 A | 10/1989 | Vilhardt |
| 4,884,579 A | 12/1989 | Engelson |
| 4,890,612 A | 1/1990 | Kensey |
| 4,913,141 A | 4/1990 | Hillstead |
| 4,923,464 A | 5/1990 | DiPisa, Jr. |
| 4,955,862 A | 9/1990 | Sepetka |
| 4,957,501 A | 9/1990 | Lahille et al. |
| 4,985,467 A | 1/1991 | Kelly et al. |
| 4,994,069 A | 2/1991 | Ritchart et al. |
| 5,002,556 A | 3/1991 | Ishida et al. |
| 5,013,316 A | 5/1991 | Goble et al. |
| 5,019,090 A | 5/1991 | Pinchuk |
| 5,035,891 A | 7/1991 | Runkel |
| 5,037,427 A | 8/1991 | Harada et al. |
| 5,061,274 A | 10/1991 | Kensey |
| 5,061,914 A | 10/1991 | Busch et al. |
| 5,062,829 A | 11/1991 | Pryor et al. |
| 5,064,434 A | 11/1991 | Haber |
| 5,092,877 A | 3/1992 | Pinchuk |
| 5,098,374 A | 3/1992 | Othel-Jacobsen et al. |
| 5,098,440 A | 3/1992 | Hillstead |
| 5,108,407 A | 4/1992 | Geremia |
| 5,108,438 A | 4/1992 | Stone |
| 5,109,867 A | 5/1992 | Twyford |
| 5,120,816 A | 6/1992 | Gould et al. |
| 5,122,136 A | 6/1992 | Guglielmi |
| 5,132,415 A | 7/1992 | Diamantoglou et al. |
| 5,133,731 A | 7/1992 | Butler |
| 5,133,742 A | 7/1992 | Pinchuk |
| 5,133,755 A | 7/1992 | Brekke |
| 5,167,624 A | 12/1992 | Butler |
| 5,174,276 A | 12/1992 | Crockard |
| 5,217,484 A | 6/1993 | Marks |
| 5,228,453 A | 7/1993 | Sepetka |
| 5,229,431 A | 7/1993 | Pinchuk |
| 5,234,437 A | 8/1993 | Sepetka |
| 5,250,071 A | 10/1993 | Palermo |
| 5,256,146 A | 10/1993 | Ensminger et al. |
| 5,258,000 A | 11/1993 | Gianturco |
| 5,261,916 A | 11/1993 | Engelson |
| 5,263,964 A | 11/1993 | Purdy |
| 5,290,295 A | 3/1994 | Querals et al. |
| 5,296,518 A | 3/1994 | Grasel et al. |
| 5,304,195 A | 4/1994 | Twyford |
| 5,308,342 A | 5/1994 | Sepetka et al. |
| 5,312,356 A | 5/1994 | Engelson et al. |
| 5,312,415 A | 5/1994 | Palermo |
| 5,318,527 A | 6/1994 | Hyde et al. |
| 5,334,210 A | 8/1994 | Gianturco |
| 5,350,397 A | 9/1994 | Palermo et al. |
| 5,354,295 A | 10/1994 | Guglielmi et al. |
| 5,356,388 A | 10/1994 | Sepetka et al. |
| 5,380,334 A | 1/1995 | Torrie et al. |
| 5,382,259 A | 1/1995 | Phelps et al. |
| 5,417,708 A | 5/1995 | Hall et al. |
| 5,423,829 A | 6/1995 | Pham |
| 5,423,849 A | 6/1995 | Engelson et al. |
| 5,429,605 A | 7/1995 | Bernd et al. |
| 5,487,385 A | 1/1996 | Avitall |
| 5,496,305 A | 3/1996 | Kittrell et al. |
| 5,514,085 A | 5/1996 | Yoon |
| 5,514,378 A | 5/1996 | Mikos et al. |
| 5,520,700 A | 5/1996 | Beyar et al. |
| 5,522,819 A | 6/1996 | Graves et al. |
| 5,522,836 A | 6/1996 | Palermo |
| 5,522,895 A | 6/1996 | Mikos |
| 5,525,348 A | 6/1996 | Whitbourne et al. |
| 5,540,680 A | 7/1996 | Guglielmi |
| 5,551,443 A | 9/1996 | Sepetka et al. |
| 5,556,429 A | 9/1996 | Felt |
| 5,562,698 A | 10/1996 | Parker |
| 5,578,074 A | 11/1996 | Mirigian |
| 5,582,619 A | 12/1996 | Ken |
| 5,601,600 A | 2/1997 | Ton |
| 5,607,474 A | 3/1997 | Athanasiou et al. |
| 5,618,314 A | 4/1997 | Harwin et al. |
| 5,624,449 A | 4/1997 | Pham |
| 5,629,008 A | 5/1997 | Lee |
| 5,634,926 A | 6/1997 | Jobe |
| 5,658,308 A | 8/1997 | Snyder |
| 5,667,513 A | 9/1997 | Torrie et al. |
| 5,677,355 A | 10/1997 | Shalaby et al. |
| 5,686,091 A | 11/1997 | Leong et al. |
| 5,690,666 A | 11/1997 | Berenstein et al. |
| 5,690,671 A | 11/1997 | McGurk et al. |
| 5,692,008 A | 11/1997 | Van Nee |
| 5,709,934 A | 1/1998 | Bell et al. |
| 5,711,960 A | 1/1998 | Shikinami |
| 5,716,413 A | 2/1998 | Walter et al. |
| 5,718,711 A | 2/1998 | Berenstein et al. |
| 5,722,989 A | 3/1998 | Fitch |
| 5,725,534 A | 3/1998 | Rasmussen |
| 5,725,546 A | 3/1998 | Samson |
| 5,725,568 A | 3/1998 | Hastings |
| 5,726,161 A | 3/1998 | Whistler |
| 5,730,757 A | 3/1998 | Benetti et al. |
| 5,741,331 A | 4/1998 | Pinchuk |
| 5,746,769 A | 5/1998 | Ton |
| 5,749,894 A | 5/1998 | Engelson |
| 5,750,585 A | 5/1998 | Park et al. |
| 5,755,774 A | 5/1998 | Pinchuk |
| 5,755,777 A | 5/1998 | Chuter |
| 5,759,161 A | 6/1998 | Ogawa |
| 5,766,160 A | 6/1998 | Samson et al. |
| 5,769,870 A | 6/1998 | Salahieh et al. |
| 5,769,899 A | 6/1998 | Schwartz et al. |
| 5,770,193 A | 6/1998 | Vacanti et al. |
| 5,776,154 A | 7/1998 | Taylor et al. |
| 5,776,184 A | 7/1998 | Tuch |
| 5,789,018 A | 8/1998 | Engelson et al. |
| 5,800,453 A | 9/1998 | Gia |
| 5,800,455 A | 9/1998 | Palermo |
| 5,814,062 A | 9/1998 | Sepetka |
| 5,820,917 A | 10/1998 | Tuch |
| 5,823,198 A | 10/1998 | Jones et al. |
| 5,824,081 A | 10/1998 | Knapp et al. |
| 5,826,587 A | 10/1998 | Berenstein et al. |
| 5,830,183 A | 11/1998 | Krieger |
| 5,833,705 A | 11/1998 | Ken et al. |
| 5,843,118 A | 12/1998 | Sepetka et al. |
| 5,846,210 A | 12/1998 | Ogawa |
| 5,851,206 A | 12/1998 | Guglielmi et al. |
| 5,853,418 A | 12/1998 | Ken et al. |
| 5,855,578 A | 1/1999 | Guglielmi |
| 5,863,627 A | 1/1999 | Szycher |
| 5,865,814 A | 2/1999 | Tuch |
| 5,865,844 A | 2/1999 | Plaia et al. |
| 5,871,496 A | 2/1999 | Ginn et al. |
| 5,882,334 A | 3/1999 | Sepetka et al. |
| 5,891,128 A | 4/1999 | Gia et al. |
| 5,891,130 A | 4/1999 | Palermo |
| 5,891,159 A | 4/1999 | Sherman et al. |
| 5,891,192 A | 4/1999 | Murayama et al. |
| 5,891,558 A | 4/1999 | Bell et al. |
| 5,894,843 A | 4/1999 | Benetti et al. |
| 5,895,385 A | 4/1999 | Guglielmi |
| 5,895,391 A | 4/1999 | Farnholtz |
| 5,895,407 A | 4/1999 | Jayaraman |
| 5,904,703 A | 5/1999 | Gilson |

| Patent No. | Date | Inventor | Patent No. | Date | Inventor |
|---|---|---|---|---|---|
| 5,911,728 A | 6/1999 | Sepetka et al. | 6,165,193 A | 12/2000 | Greene, Jr. et al. |
| 5,911,731 A | 6/1999 | Pham et al. | 6,165,212 A | 12/2000 | Dereume et al. |
| 5,916,235 A | 6/1999 | Guglielmi | 6,168,592 B1 | 1/2001 | Kupiecki et al. |
| 5,925,037 A | 7/1999 | Guglielmi | 6,168,615 B1 | 1/2001 | Ken et al. |
| 5,925,054 A | 7/1999 | Taylor et al. | 6,168,622 B1 | 1/2001 | Mazzocchi |
| 5,925,059 A | 7/1999 | Palermo | 6,169,048 B1 | 1/2001 | Sjogren et al. |
| 5,925,060 A | 7/1999 | Forber | 6,171,298 B1 | 1/2001 | Matsuura |
| 5,928,226 A | 7/1999 | Guglielmi | 6,177,522 B1 | 1/2001 | Brady et al. |
| 5,928,260 A | 7/1999 | Chin et al. | 6,183,461 B1 | 2/2001 | Matsuura et al. |
| 5,944,714 A | 8/1999 | Guglielmi | 6,183,491 B1 | 2/2001 | Lulo |
| 5,944,733 A | 8/1999 | Engelson | 6,183,518 B1 | 2/2001 | Ross et al. |
| 5,944,736 A | 8/1999 | Taylor et al. | 6,187,027 B1 | 2/2001 | Mariant et al. |
| 5,947,962 A | 9/1999 | Guglielmi | 6,190,311 B1 | 2/2001 | Glines et al. |
| 5,947,963 A | 9/1999 | Guglielmi | 6,190,357 B1 | 2/2001 | Ferrari et al. |
| 5,951,539 A | 9/1999 | Nita et al. | 6,190,373 B1 | 2/2001 | Palermo |
| 5,962,620 A | 10/1999 | Reich et al. | 6,193,708 B1 | 2/2001 | Ken et al. |
| 5,968,078 A | 10/1999 | Grotz | RE37,117 E | 3/2001 | Palermo |
| 5,976,126 A | 11/1999 | Guglielmi | 6,197,240 B1 | 3/2001 | Pinchuk |
| 5,984,929 A | 11/1999 | Bashiri | 6,203,547 B1 | 3/2001 | Nguyen |
| 5,986,034 A | 11/1999 | DiDomenico et al. | 6,207,180 B1 | 3/2001 | Ottoboni et al. |
| 5,989,242 A | 11/1999 | Saadat | 6,213,941 B1 | 4/2001 | Benetti et al. |
| 6,001,111 A | 12/1999 | Sepetka et al. | 6,214,002 B1 | 4/2001 | Fleischman et al. |
| 6,010,498 A | 1/2000 | Guglielmi | 6,214,022 B1 | 4/2001 | Taylore et al. |
| 6,011,995 A | 1/2000 | Guglielmi et al. | 6,221,061 B1 | 4/2001 | Engelson et al. |
| 6,015,422 A | 1/2000 | Kerr | 6,221,066 B1 | 4/2001 | Ferreral et al. |
| 6,015,424 A | 1/2000 | Rosenbluth et al. | 6,224,610 B1 | 5/2001 | Ferrera |
| 6,019,757 A | 2/2000 | Scheldrup | 6,224,630 B1 | 5/2001 | Bao et al. |
| 6,019,771 A | 2/2000 | Bennett et al. | 6,231,586 B1 | 5/2001 | Mariant |
| 6,022,340 A | 2/2000 | Sepetka et al. | 6,231,590 B1 | 5/2001 | Slaikeu et al. |
| 6,024,754 A | 2/2000 | Engelson | 6,231,879 B1 | 5/2001 | Li et al. |
| 6,033,423 A | 3/2000 | Ken et al. | 6,238,403 B1 | 5/2001 | Greene, Jr. et al. |
| 6,036,706 A | 3/2000 | Morejohn et al. | 6,238,415 B1 | 5/2001 | Sepetka et al. |
| 6,036,720 A | 3/2000 | Abrams et al. | 6,245,090 B1 | 6/2001 | Gilson et al. |
| 6,039,967 A | 3/2000 | Ottoboni | 6,245,107 B1 | 6/2001 | Ferree |
| 6,042,563 A | 3/2000 | Morejohn et al. | 6,254,592 B1 | 7/2001 | Samson et al. |
| 6,042,592 A | 3/2000 | Schmitt | 6,258,055 B1 | 7/2001 | McCrory et al. |
| 6,048,333 A | 4/2000 | Lennox et al. | 6,270,456 B1 | 8/2001 | Iliff |
| 6,050,266 A | 4/2000 | Benetti et al. | 6,270,465 B1 | 8/2001 | Keith et al. |
| 6,054,142 A | 4/2000 | Li et al. | 6,273,897 B1 | 8/2001 | Dalessandro et al. |
| 6,063,070 A | 5/2000 | Eder | 6,277,125 B1 | 8/2001 | Barry |
| 6,063,100 A | 5/2000 | Diaz | 6,277,126 B1 | 8/2001 | Barry |
| 6,063,104 A | 5/2000 | Villar et al. | 6,280,455 B1 | 8/2001 | Ginn et al. |
| 6,063,395 A | 5/2000 | Markkula | 6,280,457 B1 | 8/2001 | Wallace et al. |
| 6,066,133 A | 5/2000 | Guglielmi | 6,290,691 B1 | 9/2001 | Krieger |
| 6,068,644 A | 5/2000 | Lulo | 6,293,923 B1 | 9/2001 | Yachia |
| 6,071,297 A | 6/2000 | Salahieh et al. | 6,296,622 B1 | 10/2001 | Kurz |
| 6,077,260 A | 6/2000 | Wheelock | 6,299,619 B1 | 10/2001 | Greene, Jr. et al. |
| 6,083,220 A | 7/2000 | Guglielmi | 6,306,153 B1 | 10/2001 | Kurz et al. |
| 6,086,591 A | 7/2000 | Bojarski | 6,306,159 B1 | 10/2001 | Schwartz et al. |
| 6,093,199 A | 7/2000 | Brown et al. | 6,306,424 B1 | 10/2001 | Vyakarnam et al. |
| 6,096,060 A | 8/2000 | Fitts et al. | 6,309,413 B1 | 10/2001 | Dereume et al. |
| 6,099,562 A | 8/2000 | Ding et al. | 6,312,421 B1 | 11/2001 | Boock |
| 6,102,917 A | 8/2000 | Maitland | 6,313,254 B1 | 11/2001 | Meijs et al. |
| 6,102,932 A | 8/2000 | Kurz | 6,315,717 B1 | 11/2001 | Benetti et al. |
| 6,102,939 A | 8/2000 | Pinchuk | 6,319,267 B1 | 11/2001 | Kurz |
| 6,110,190 A | 8/2000 | Ginn et al. | 6,322,576 B1 | 11/2001 | Wallace et al. |
| 6,111,052 A | 8/2000 | DiDomenico et al. | 6,333,029 B1 | 12/2001 | Vyakarnam et al. |
| 6,113,616 A | 9/2000 | Taylor et al. | 6,335,384 B1 | 1/2002 | Evans et al. |
| 6,113,622 A | 9/2000 | Hieshima | 6,344,035 B1 | 2/2002 | Chudzik et al. |
| 6,113,629 A | 9/2000 | Ken | 6,344,048 B1 | 2/2002 | Chin et al. |
| 6,117,142 A | 9/2000 | Goodson | 6,346,077 B1 | 2/2002 | Taylor et al. |
| 6,117,441 A | 9/2000 | Moo-Young | 6,346,117 B1 | 2/2002 | Greenhalgh |
| 6,123,714 A | 9/2000 | Gia et al. | 6,355,030 B1 | 3/2002 | Aldrich et al. |
| 6,135,193 A | 10/2000 | Lloyd | 6,355,063 B1 | 3/2002 | Calcote |
| 6,136,015 A | 10/2000 | Kurz et al. | 6,355,699 B1 | 3/2002 | Vyakarnam et al. |
| 6,139,510 A | 10/2000 | Palermo | 6,361,547 B1 | 3/2002 | Hieshima |
| 6,139,520 A | 10/2000 | McCrory et al. | 6,365,149 B2 | 4/2002 | Vyakarnam et al. |
| 6,139,535 A | 10/2000 | Greelis | 6,368,338 B1 | 4/2002 | Konya et al. |
| 6,139,564 A | 10/2000 | Teoh | 6,372,228 B1 | 4/2002 | Gregory |
| 6,149,664 A | 11/2000 | Kurz | 6,375,662 B1 | 4/2002 | Schmitt |
| 6,149,678 A | 11/2000 | DiDomenico et al. | 6,375,668 B1 | 4/2002 | Gifford et al. |
| 6,153,292 A | 11/2000 | Bell et al. | 6,375,669 B1 | 4/2002 | Rosenbluth et al. |
| 6,159,165 A | 12/2000 | Ferrera et al. | 6,379,329 B1 | 4/2002 | Naglreiter et al. |

| Patent No. | Date | Inventor |
|---|---|---|
| 6,379,373 B1 | 4/2002 | Sawhney et al. |
| 6,379,374 B1 | 4/2002 | Hieshima |
| 6,383,171 B1 | 5/2002 | Gifford et al. |
| 6,387,108 B1 | 5/2002 | Taylor et al. |
| 6,394,951 B1 | 5/2002 | Taylor et al. |
| 6,398,718 B1 | 6/2002 | Yachia et al. |
| 6,402,750 B1 | 6/2002 | Atkinson et al. |
| 6,409,721 B1 | 6/2002 | Wheelock |
| 6,420,452 B1 | 7/2002 | Gunatillake et al. |
| 6,425,893 B1 | 7/2002 | Guglielmi |
| 6,425,919 B1 | 7/2002 | Lambrecht |
| 6,428,557 B1 | 8/2002 | Hilaire |
| 6,428,558 B1 | 8/2002 | Jones et al. |
| 6,428,576 B1 | 8/2002 | Haldimann |
| 6,430,426 B2 | 8/2002 | Avitall |
| 6,432,122 B1 | 8/2002 | Gilson et al. |
| 6,436,135 B1 | 8/2002 | Goldfarb |
| 6,437,073 B1 | 8/2002 | Gunatillake et al. |
| 6,448,049 B1 | 9/2002 | Tsutsumi et al. |
| 6,454,780 B1 | 9/2002 | Wallace |
| 6,454,811 B1 | 9/2002 | Sherwood et al. |
| 6,458,119 B1 | 10/2002 | Berenstein et al. |
| 6,458,127 B1 | 10/2002 | Truckai et al. |
| 6,475,232 B1 | 11/2002 | Babbs et al. |
| 6,478,773 B1 | 11/2002 | Gandhi |
| 6,482,235 B1 | 11/2002 | Lambrecht et al. |
| 6,485,575 B2 | 11/2002 | Yuan |
| 6,494,884 B2 | 12/2002 | Gifford |
| 6,500,149 B2 | 12/2002 | Gandhi |
| 6,500,190 B2 | 12/2002 | Greene, Jr. et al. |
| 6,506,204 B2 | 1/2003 | Mazzocchi |
| 6,514,264 B1 | 2/2003 | Naglreiter |
| 6,514,280 B1 | 2/2003 | Gilson |
| 6,530,934 B1 | 3/2003 | Jacobsen et al. |
| 6,531,154 B1 | 3/2003 | Mathiowitz et al. |
| 6,537,569 B2 | 3/2003 | Cruise |
| 6,544,225 B1 | 4/2003 | Lulo |
| 6,544,262 B2 | 4/2003 | Fleischman |
| 6,545,097 B2 | 4/2003 | Pinchuk et al. |
| 6,554,842 B2 | 4/2003 | Heuser et al. |
| 6,569,653 B1 | 5/2003 | Alard et al. |
| 6,578,580 B2 | 6/2003 | Conrad et al. |
| 6,579,291 B1 | 6/2003 | Keith et al. |
| 6,589,199 B1 | 7/2003 | McCrory et al. |
| 6,589,230 B2 | 7/2003 | Gia et al. |
| 6,589,265 B1 | 7/2003 | Palmer et al. |
| 6,592,625 B2 | 7/2003 | Cauthen |
| 6,599,323 B2 | 7/2003 | Melican et al. |
| 6,602,189 B1 | 8/2003 | Bennetti et al. |
| 6,602,261 B2 | 8/2003 | Greene, Jr. et al. |
| 6,602,291 B1 | 8/2003 | Ray et al. |
| 6,605,101 B1 | 8/2003 | Schaefer et al. |
| 6,607,538 B1 | 8/2003 | Ferrera et al. |
| 6,610,317 B2 | 8/2003 | Straub et al. |
| 6,616,617 B1 | 9/2003 | Ferrera et al. |
| 6,617,014 B1 | 9/2003 | Thomson |
| 6,620,152 B2 | 9/2003 | Guglielmi |
| 6,623,493 B2 | 9/2003 | Wallace et al. |
| 6,635,068 B1 | 10/2003 | Dubrul et al. |
| 6,636,758 B2 | 10/2003 | Sanchez et al. |
| 6,638,243 B2 | 10/2003 | Kupiecki |
| 6,638,245 B2 | 10/2003 | Miller et al. |
| 6,638,293 B1 | 10/2003 | Makower et al. |
| 6,638,312 B2 | 10/2003 | Plouhar et al. |
| 6,656,201 B2 | 12/2003 | Ferrera et al. |
| 6,663,650 B2 | 12/2003 | Sepetka et al. |
| 6,664,389 B1 | 12/2003 | Shi et al. |
| 6,669,706 B2 | 12/2003 | Schmitt et al. |
| 6,673,013 B2 | 1/2004 | Benetti et al. |
| 6,673,285 B2 | 1/2004 | Ma |
| 6,679,903 B2 | 1/2004 | Kurz |
| 6,689,125 B1 | 2/2004 | Keith et al. |
| 6,689,141 B2 | 2/2004 | Ferrera |
| 6,692,510 B2 | 2/2004 | West |
| 6,701,930 B2 | 3/2004 | Benetti et al. |
| 6,702,782 B2 | 3/2004 | Miller et al. |
| 6,706,025 B2 | 3/2004 | Engelson et al. |
| 6,712,842 B1 | 3/2004 | Gifford, III et al. |
| 6,723,108 B1 | 4/2004 | Jones et al. |
| 6,723,112 B2 | 4/2004 | Ho et al. |
| 6,726,621 B2 | 4/2004 | Suon et al. |
| 6,730,104 B1 | 5/2004 | Sepetka et al. |
| 6,743,169 B1 | 6/2004 | Taylor et al. |
| 6,743,236 B2 | 6/2004 | Barry |
| 6,746,467 B1 | 6/2004 | Taylor et al. |
| 6,746,468 B1 | 6/2004 | Sepetka et al. |
| 6,780,196 B2 | 8/2004 | Chin et al. |
| 6,784,273 B1 | 8/2004 | Spaans et al. |
| 6,811,560 B2 | 11/2004 | Jones et al. |
| 6,811,561 B2 | 11/2004 | Diaz |
| 6,824,545 B2 | 11/2004 | Sepetka et al. |
| 6,824,550 B1 | 11/2004 | Noriega et al. |
| 6,835,185 B2 | 12/2004 | Ramzipoor |
| 6,846,328 B2 | 1/2005 | Cauthen |
| 6,849,081 B2 | 2/2005 | Sepetka et al. |
| 6,852,330 B2 | 2/2005 | Bowman et al. |
| 6,872,218 B2 | 3/2005 | Ferrera et al. |
| 6,884,428 B2 | 4/2005 | Binette et al. |
| 6,893,464 B2 | 5/2005 | Kiester |
| 6,905,503 B2 | 6/2005 | Gifford |
| 6,953,473 B2 | 10/2005 | Porter |
| 6,958,068 B2 | 10/2005 | Hieshima |
| 6,966,892 B2 | 11/2005 | Gandhi et al. |
| 6,984,247 B2 | 1/2006 | Cauthen |
| 6,994,711 B2 | 2/2006 | Hieshima |
| 6,994,717 B2 | 2/2006 | Konya et al. |
| 6,997,929 B2 | 2/2006 | Manzi et al. |
| 7,008,979 B2 | 3/2006 | Schottman et al. |
| 7,018,394 B2 | 3/2006 | Diaz |
| 7,025,982 B2 | 4/2006 | Mattes et al. |
| 7,029,487 B2 | 4/2006 | Greene |
| 7,033,388 B2 | 4/2006 | Zilla et al. |
| 7,044,962 B2 * | 5/2006 | Elliott .................. 623/1.13 |
| 7,112,417 B2 | 9/2006 | Vyakarnam et al. |
| 7,128,736 B1 | 10/2006 | Abrams et al. |
| 7,147,618 B2 | 12/2006 | Kurz |
| 7,160,333 B2 | 1/2007 | Plouhar |
| 7,179,276 B2 | 2/2007 | Barry |
| 7,182,774 B2 | 2/2007 | Barry |
| 7,192,604 B2 | 3/2007 | Brown et al. |
| 7,198,613 B2 | 4/2007 | Gandhi |
| 7,255,707 B2 | 8/2007 | Ramzipoor |
| 7,323,000 B2 | 1/2008 | Monstdt |
| 2001/0002438 A1 | 5/2001 | Sepetka |
| 2001/0016738 A1 | 8/2001 | Harrington et al. |
| 2001/0019719 A1 | 9/2001 | Ottoboni et al. |
| 2001/0044572 A1 | 11/2001 | Benetti et al. |
| 2001/0049521 A1 | 12/2001 | Gia et al. |
| 2002/0002383 A1 | 1/2002 | Sepetka et al. |
| 2002/0005600 A1 | 1/2002 | Ma |
| 2002/0010388 A1 | 1/2002 | Taylor et al. |
| 2002/0018795 A1 | 2/2002 | Whitbourne |
| 2002/0018884 A1 | 2/2002 | Thomson |
| 2002/0040182 A1 | 4/2002 | Benetti et al. |
| 2002/0055730 A1 | 5/2002 | Yachia et al. |
| 2002/0055786 A1 | 5/2002 | Atala |
| 2002/0072550 A1 | 6/2002 | Brady et al. |
| 2002/0072764 A1 | 6/2002 | Sepetka et al. |
| 2002/0072791 A1 | 6/2002 | Eder |
| 2002/0091380 A1 | 7/2002 | Wheelock |
| 2002/0099270 A1 | 7/2002 | Taylor et al. |
| 2002/0099408 A1 | 7/2002 | Marks |
| 2002/0101008 A1 | 8/2002 | Sokolowski |
| 2002/0107330 A1 | 8/2002 | Pinchuk et al. |
| 2002/0111646 A1 | 8/2002 | Gifford, III et al. |
| 2002/0119177 A1 | 8/2002 | Bowman et al. |

| | | | | | | |
|---|---|---|---|---|---|---|
| 2002/0120348 A1 | 8/2002 | Melican et al. | | 2005/0085849 A1 | 4/2005 | Sepetka et al. |
| 2002/0123738 A1 | 9/2002 | Jansen et al. | | 2005/0125024 A1 | 6/2005 | Sepetka et al. |
| 2002/0123765 A1 | 9/2002 | Sepetka et al. | | 2005/0149046 A1 | 7/2005 | Friedman et al. |
| 2002/0133189 A1 | 9/2002 | Gifford, III et al. | | 2005/0149108 A1 | 7/2005 | Cox |
| 2002/0133190 A1 | 9/2002 | Horton et al. | | 2005/0149197 A1 | 7/2005 | Cauthen |
| 2002/0138096 A1 | 9/2002 | Hieshima et al. | | 2005/0154417 A1 | 7/2005 | Sepetka |
| 2002/0142413 A1 | 10/2002 | Brady et al. | | 2005/0154463 A1 | 7/2005 | Trieu |
| 2002/0143349 A1 | 10/2002 | Gifford, III et al. | | 2005/0165480 A1 | 7/2005 | Jordan et al. |
| 2002/0165450 A1 | 11/2002 | Sanchez et al. | | 2005/0171572 A1 | 8/2005 | Martinez |
| 2002/0169066 A1 | 11/2002 | Cassidy et al. | | 2005/0177237 A1 | 8/2005 | Shappley et al. |
| 2002/0169473 A1 | 11/2002 | Sepetka et al. | | 2005/0182418 A1 | 8/2005 | Boyd |
| 2002/0169495 A1 | 11/2002 | Gifford et al. | | 2005/0209696 A1 | 9/2005 | Lin et al. |
| 2002/0169497 A1 | 11/2002 | Wholey et al. | | 2005/0216030 A1 | 9/2005 | Sepetka et al. |
| 2002/0169499 A1 | 11/2002 | Zilla et al. | | 2005/0216050 A1 | 9/2005 | Sepetka et al. |
| 2002/0172717 A1 | 11/2002 | Leong et al. | | 2005/0222580 A1 | 10/2005 | Gifford, III et al. |
| 2002/0173851 A1 | 11/2002 | McKay | | 2005/0222662 A1 | 10/2005 | Thompson |
| 2002/0177870 A1 | 11/2002 | Sepetka et al. | | 2005/0245882 A1 | 11/2005 | Elkins et al. |
| 2002/0183858 A1 | 12/2002 | Contiliano et al. | | 2005/0246021 A1 | 11/2005 | Ringeisen et al. |
| 2002/0188311 A1 | 12/2002 | Ferrera | | 2005/0251200 A1 | 11/2005 | Porter |
| 2002/0198491 A1 | 12/2002 | Miller et al. | | 2005/0288686 A1 | 12/2005 | Sepetka et al. |
| 2002/0198492 A1 | 12/2002 | Miller et al. | | 2006/0015182 A1* | 1/2006 | Tsou ........................ 623/17.11 |
| 2002/0198599 A1 | 12/2002 | Haldimann | | 2006/0025801 A1 | 2/2006 | Lulo |
| 2003/0008015 A1 | 1/2003 | Levisage et al. | | 2006/0025802 A1 | 2/2006 | Sowers |
| 2003/0014073 A1 | 1/2003 | Bashiri | | 2006/0025803 A1 | 2/2006 | Mitelberg |
| 2003/0014075 A1 | 1/2003 | Rosenbluth et al. | | 2006/0030814 A1 | 2/2006 | Valencia et al. |
| 2003/0014118 A1 | 1/2003 | Lambrecht et al. | | 2006/0030939 A1 | 2/2006 | Frank |
| 2003/0051735 A1 | 3/2003 | Pavcnik et al. | | 2006/0036218 A1 | 2/2006 | Goodson et al. |
| 2003/0074075 A1 | 4/2003 | Thomas, Jr. et al. | | 2006/0052814 A1 | 3/2006 | Sater |
| 2003/0100920 A1 | 5/2003 | Akin et al. | | 2006/0052815 A1 | 3/2006 | Fitz |
| 2003/0120261 A1 | 6/2003 | Gellman | | 2006/0052816 A1 | 3/2006 | Bates |
| 2003/0120345 A1 | 6/2003 | Cauthen | | 2006/0069323 A1 | 3/2006 | Elkins et al. |
| 2003/0130689 A1 | 7/2003 | Wallace et al. | | 2006/0106420 A1 | 5/2006 | Dolan et al. |
| 2003/0153976 A1 | 8/2003 | Cauthen, III et al. | | 2006/0116709 A1 | 6/2006 | Sepetka et al. |
| 2003/0171739 A1 | 9/2003 | Murphy et al. | | 2006/0116712 A1 | 6/2006 | Sepetka et al. |
| 2003/0171773 A1 | 9/2003 | Carrison | | 2006/0116713 A1 | 6/2006 | Sepetka et al. |
| 2003/0193104 A1 | 10/2003 | Melican | | 2006/0116714 A1 | 6/2006 | Sepetka et al. |
| 2003/0195560 A1 | 10/2003 | Ginn | | 2006/0195137 A1 | 8/2006 | Sepetka et al. |
| 2003/0199887 A1 | 10/2003 | Ferrera et al. | | 2006/0200192 A1 | 9/2006 | Fitz |
| 2003/0204246 A1 | 10/2003 | Chu et al. | | 2006/0265044 A1 | 11/2006 | Gifford, III et al. |
| 2003/0208259 A1 | 11/2003 | Penhasi | | 2006/0282112 A1 | 12/2006 | Griffin |
| 2003/0215564 A1 | 11/2003 | Heller et al. | | 2007/0118172 A1 | 5/2007 | Balgobin |
| 2003/0220690 A1 | 11/2003 | Cauthen, III | | 2007/0270903 A1 | 11/2007 | Davis |
| 2004/0039392 A1* | 2/2004 | Trieu ........................ 606/86 | | 2007/0293930 A1 | 12/2007 | Wang |
| 2004/0068314 A1 | 4/2004 | Jones et al. | | 2008/0027482 A1 | 1/2008 | Sekido |
| 2004/0073243 A1 | 4/2004 | Sepetka et al. | | 2008/0045997 A1 | 2/2008 | Balgobin |
| 2004/0078077 A1 | 4/2004 | Binette et al. | | | | |
| 2004/0079429 A1 | 4/2004 | Miller et al. | | | FOREIGN PATENT DOCUMENTS | |
| 2004/0087834 A1 | 5/2004 | Benetti et al. | | EP | 0274898 | 7/1988 |
| 2004/0098024 A1 | 5/2004 | Dieck et al. | | EP | 0572932 | 12/1993 |
| 2004/0115164 A1 | 6/2004 | Pierce et al. | | EP | 0649288 | 12/1993 |
| 2004/0133233 A1 | 7/2004 | Sepetka et al. | | EP | 0598025 | 5/1994 |
| 2004/0158282 A1 | 8/2004 | Jones et al. | | EP | 0601044 | 6/1994 |
| 2004/0161451 A1 | 8/2004 | Pierce et al. | | EP | 0606392 | 7/1994 |
| 2004/0162519 A1 | 8/2004 | Helkowski et al. | | EP | 0615459 | 9/1994 |
| 2004/0167534 A1 | 8/2004 | Errico et al. | | EP | 0617632 | 10/1994 |
| 2004/0175408 A1 | 9/2004 | Chun et al. | | EP | 0681492 | 7/1995 |
| 2004/0181253 A1 | 9/2004 | Sepetka et al. | | EP | 0693948 | 12/1995 |
| 2004/0193246 A1 | 9/2004 | Ferrera | | EP | 0703798 | 4/1996 |
| 2004/0204701 A1 | 10/2004 | Cox | | EP | 0711532 | 5/1996 |
| 2004/0220563 A1 | 11/2004 | Eder | | EP | 0754435 | 1/1997 |
| 2004/0230099 A1 | 11/2004 | Taylor et al. | | EP | 0765636 | 4/1997 |
| 2004/0230285 A1 | 11/2004 | Gifford, III et al. | | EP | 0778005 | 6/1997 |
| 2004/0265880 A1 | 12/2004 | Donahue et al. | | EP | 0847772 | 6/1998 |
| 2005/0021023 A1 | 1/2005 | Guglielmi | | EP | 0853955 | 7/1998 |
| 2005/0021077 A1 | 1/2005 | Chin et al. | | EP | 0616543 | 9/1998 |
| 2005/0033348 A1 | 2/2005 | Sepetka et al. | | EP | 0970704 | 1/2000 |
| 2005/0033350 A1 | 2/2005 | Ken et al. | | EP | 0820726 | 9/2003 |
| 2005/0043585 A1 | 2/2005 | Datta et al. | | EP | 1202683 | 5/2006 |
| 2005/0043780 A1 | 2/2005 | Gifford et al. | | WO | WO 94/06460 | 3/1994 |
| 2005/0043816 A1 | 2/2005 | Datta et al. | | WO | WO 98/46287 | 10/1998 |
| 2005/0049619 A1 | 3/2005 | Sepetka et al. | | WO | WO 99/05977 | 2/1999 |
| 2005/0059995 A1 | 3/2005 | Sepetka et al. | | WO | WO 99/23954 | 5/1999 |
| 2005/0060022 A1 | 3/2005 | Felt et al. | | | | |

| WO | WO 99/24084 | 5/1999 |
| WO | WO 99/24106 | 5/1999 |
| WO | WO 99/61084 | 12/1999 |
| WO | WO 00/07524 | 2/2000 |
| WO | WO 01/03607 | 1/2001 |
| WO | WO 01/21108 | 3/2001 |
| WO | WO 01/74582 A1 | 10/2001 |
| WO | WO 2004/002351 | 1/2004 |
| WO | WO 2004/062531 | 7/2004 |
| WO | WO 2006/088531 | 8/2006 |

OTHER PUBLICATIONS

Ahlgren, et al., Anular Incision Technique on the Strength and Multidirectional Flexibility of the HEaling Intervertebral Disc, Spine, vol. 19, No. 8, pp. 948-954 (1994).

Ahlgren, et al., Effect of Anular Repair on the Healing Strength of the Intervertebral Disc, Spine, vol. 25, No. 17, pp. 2165-2170 (2000).

U.S. Appl. No. 60/471,520, filed May 15, 2003, Constantino et al.

Bioabsorbable Polymers, <<http://courses.abc.umn.edu/medical-school/BMEn/5001/notes/bioabs.html>>, pp. 1-8.

Gianturco-Grifka Vascular Occlusion Devices, <<www.cookmedical.com/di/dataSheet.do?id=39>>, 2006.

Pediatric Cardiology, <<www.egyptheart.org/EHJ1/JESPC1/jespc02.htm>> The Egyptian Society of Pediatric Cardiologists, vol. 1(2), pp. 1-18, Dec. 1997.

B.W. Sauer et al., Porous High Density Polyethylene (PHDPE)—Autogenous Tissue Tracheal, Trans Am. Soc. Artif. Intern. Organs, vol. 28, pp. 369-373, Apr. 14-16.

Barone et al., The Biomechanical and Histopathologic Effects of Surface Texturing with Silicone and Polyurethane in Tissue Implantation and Expansion, Plast. Reconstr. Surg., vol. 90(1), pp. 77-86, 1992.

Berghaus et al., Porose Kunststoffe Fur die Ohrmuschelplastik, Larvng. Rhinol. Otol., vol. 62, pp. 320-327, 1983.

Bettina Marty et al., Biologic Fixation of Polyester-versus Polyurethane-covered Stents in a Porcine Model, Laboratory Investigations, vol. 13(6), pp. 601-607, Jun. 2002.

Campbell et al., Microtopography and Soft Tissue Response, J. Investigative Surgery, vol. 2, pp. 51-74, 1989.

Clarke et al., Innovative Manufacture of Olefin Foams, Paper 17 in the proceedings of Blowing Agents and Foaming Processes, Munich Germany, 2006.

David J. Mooney et al., Novel Approach to Fabricate Porous Sponges of poly(D,L-lactic-co-glycolic acid) without the use of organic solvents, Biomaterials, vol. 17, pp. 1417-1422, 1996.

Eugene Whilte et al., Biomaterial Aspects of Interpore-200 Porous Hydroxyapatite, Dental Clinics of North America, vol. 30(1), pp. 49-67, Jan. 1986.

Fraser et al., The Future of Bladder Control—Intravesical Drug Delivery, a Pinch of Pepper and Gene Therapy, Reviews in Urology, vol. 4(1), pp. 1-11, 2002.

Green, Reticulated Foams, Encyclopedia of Polymer Science and Technology, vol. 12, pp. 102-104, 1970.

Hugh U. Cameron, Essential Design Consideratins for Microporous Implants: Preliminary Communication, Journal of the Royal Society of Medicine, vol. 74, pp. 887-891, Dec. 1981.

Kang Moo Huh et al, PLGA-PEG Copolymers, <<www.drugdeliverytech.com/cgi-bin/articles.cgi?idArticle=152>>, pp. 1-11.

M. Conley Wake et al., Pore Morphology Effects on the Fibrovascular Tissue Growth in Porous Polymer Substrates, Cell Transplantation, vol. 3(4), pp. 339-343, 1994.

Macha et al., A Phorbid 20-Homovanillates Induce Apoptosis Through a VRI-Independent Mechanism, Chem. Biol., vol. 7(7), 2000.

Marshall Hicks et al., Interventional Radiology for the Cancer Patient, Principles of Imaging, pp. 440447.

Metcalfe et al., Cold Hibernated Elastic Memory Foams for Endovascular Interventions, Biomaterials, vol. 24, pp. 491-497, 2003.

Mikos et al., Laminated Three-Dimensional Biodegradable Foams for Use in Tissue Engineering, <<www.ncbi.nlm.nih.gov/entrez/query.fcgi?cmd=Retrieve&db=pubmed&list_uids=85...>>, Abstract, 1993.

Mohnaty et al., Evaluation of Soft Tissue Response to a Poly(urethane urea), Biomaterials, vol. 13(10), pp. 651-656, 1992.

Morehead et al., Soft-Tissue Response to Synthetic Biomaterials, Otolaryngologic Clinics of North Americas, vol. 27(1), pp. 195-201, 1994.

Murphy et al., Salt-Fusion: An Approach to Improve Pore Interconnectivity within Tissue Engineering Scaffolds, Tissue Engineering, vol. 8(1), pp. 43-52, 2002.

Olah et al., Ligand-induced Dynamic Membrane Changes and Cell Deletion Conferred by Vanilloid Receptor 1, The Journal of Biological Chemistry, vol. 276(14), pp. 11021-11030, 2001.

Paul S. Schreuders et al., Normal Wound Healing Compared to Healing with Porous Dacron Implants, Journal of Biomedical Materials Research, vol. 22(2), pp. 121-135, Feb. 1988.

Peter A.D. Rubin et al., Comparison of Fibrovascular Ingrowth into Hydroxyapatite and Porous Polyethylene Orbital Implants, Ophthalmic Plastics and Reconstructive Surgery, vol. 10(2), pp. 96-103, Nov. 2, 1994.

Peter J. van Mullem et al., Bone and Soft Connective Tissue Response to Porous Acrylic Implants, J. Cranio-Max.—Fac. Surg., vol. 16, pp. 99-109, 1988.

Pinchuk, A Review of the Biostability and Carcinogenecity of Polyurethanes in Medicine and the New Generation of 'Biostable' Polyurethanes, J. Biomater.Sci.Polymer Edn., vol. 6(3), pp. 225-267, 1994.

Ralph E. Holmes et al., Porous Hydroxyapatite as a Bone Graft Substitute in Diaphyseal Defects: A Histomeric Study, Journal of Orthopaedic Research, vol. 5, pp. 114-121, 1987.

Richard J. Klasa et al., Eradication of Human Non-Hodgkin's Lymphoma in SCID Mice by BCL-2 Antisense Oligonucleotides Combined with Low-Dose Cyclophosphamide, Clinical Cancer Research, vol. 6, pp. 2492-2500, Jun. 2000.

Robert M. Brohim et al., Early Tissue Reaction to Texture Breast Implant Surfaces, Annals of Plastic Surgery, vol. 28(4), pp. 354-362, Apr. 1992.

Schuber et al., Role of Oxygen in Biodegradation of Poly(etherurethane urea) Elastomers, Journal of Biomedical Materials Research, vol. 34, pp. 519-530, 1997.

Shoufeng Yang et al., The Design of Scaffolds for Use in Tissue Engineering. Part I. Traditional Factors, Tissue Engineering, vol. 7, pp. 679-689, Nov. 6, 2001.

Song et al., Bladder Tissue Pharmacokinetics of Intravesical Taxol, Cancer Chemother Pharmacol, vol. 40, pp. 285-292, 1997.

Stock et al., Tissue Engineering of Caridac Valves on the Basis of PGA/PLA Co-Polymers, <<www.ncbi.nlm.nih.gov/entrez/query.fcgi?cmd=Retrieve&db=pubmed&dopt=abstr...>>, pp. 1-2, 2001.

Stokes et al., Polyurethane Elastomer Biostability, Journal of Biomedical Materials Applications, vol. 9, pp. 321-354, 350, 1995.

Szallasi et al., A Vanilloid (Capsion) Receptors and Mechanisms, Pharmacol. Rev., vol. 51, pp. 159, 1991.

Szallas et al., A Resiniferatoxin-type Phorbid Vanillolds Display Capsaicin-like Selectivity at Native Vanilloid Receptors on Rat DR6 Neurons and at the Cloned Vanilloid Receptor VR1, vol. 128(2), pp. 428-434, 1999.

Szycher, Prosthetic and Biomedical Devices, Encyclopedia of Chemical , Technology 4th ed., vol. 20, pp. 351-395, 1996.

Vert et al., Biodegradation of PLA/GA Polymers: Increasing Complexity, <<www.ncbi.nlm.nih.gov/entrez/query.fcgi?cmd=Retrieve&db=pubmed&dopt=abstr...>>, 1994.

Ward et al., The Effect of Microgeometry, Implant Thickness and Polyurethane Chemistry on the Foreign Body Response to Subcutaneous Implants, Biomaterials, vol. 23, pp. 4185-4192, 2002.

William J. Rashking et al., Nonsurgical Closure of Patent Ductus Arteriosus: Clinical Application of the Rashkind PDA Occluder System, Circulation, vol. 75(3), pp. 583-592, Mar. 1987.

Yang et al., The Design of Scaffolds for Use in Tissue Engineering, Part 1 Traditional Factors, Tissue Engineering, vol. 7(6), pp. 679-689, 2001.

* cited by examiner

REPAIR OF SPINAL ANNULAR DEFECTS AND ANNULO-NUCLEOPLASTY REGENERATION

FIELD OF THE INVENTION

This invention relates to the repair of spinal annular defects. More particularly, this invention relates to a method and composition for the repair of spinal annular defects and annulo-nucleoplasty regeneration.

BACKGROUND OF THE INVENTION

Back pain is one of the most common and often debilitating conditions affecting millions of people. Some forms of back pain are muscular in nature and may be simply treated by rest, posture adjustments and painkillers. For example, lower back pain (LBP) is a very common condition that may be caused by unusual exertion or injury. Unusual exertion such as heavy lifting or strenuous exercise may result in back pain due to a pulled muscle, a sprained muscle, a sprained ligament, a muscle spasm, or a combination thereof. An injury caused by falling down or a blow to the back may cause bruising. These forms of back pain are typically non-chronic and may be self-treated and cured in a few days or weeks.

Other types of non-chronic back pain may be treated by improvements in physical condition, posture and/or work conditions. Being pregnant or otherwise being significantly overweight may cause LBP. A mattress that does not provide adequate support may cause back pain in the morning. Working in an environment lacking good ergonomic design may also cause back pain. In these instances, the back pain may be cured by eliminating the underlying cause. Whether it is excess body weight, a bad mattress, or a bad office chair, these forms of back pain are readily treated.

It is estimated that over ten million people in the United States alone suffer from persistent back pain. Approximately half of those suffering from persistent back pain are afflicted with chronic disabling pain, which seriously compromises a person's quality of life and is the second most common cause of worker absenteeism. Further, the cost of treating chronic back pain is very high, even though the majority of sufferers do not receive treatment due to health risks, limited treatment options, and/or inadequate therapeutic results. Thus, chronic back pain has a significantly adverse effect on a person's quality of life, on industrial productivity, and on heath care expenditures.

Some forms of back pain are the result of disorders directly related to the spinal column, which disorders are not readily treated. While some pain-causing spinal disorders may be due to facet joint degradation or degradation of individual vertebral masses, disorders associated with the intervertebral discs are predominantly affiliated with chronic back pain (referred to as disc related pain). The exact origin of disc related pain is often uncertain, and although some episodes of disc related pain may be eased with conservative treatments such as bedrest and physical therapy, future episodes of disc related pain are likely to occur periodically.

There are a number of suspected causes of disc related pain, and in any given patient, one or more of these causes may be present. However, the ability to accurately diagnose a specific cause or locus of pain is currently difficult. Because of this uncertainty, many of the causes of disc related pain are often lumped together and referred to as degenerative disc disease (DDD).

A commonly suspected source of disc related pain is physical impingement of the nerve roots emanating from the spinal cord. Such nerve root impingement may have a number of different underlying causes, but nerve root impingement generally results from either a disc protrusion or a narrowing of the intervertebral foramina (which surround the nerve roots).

As a person ages, their intervertebral discs become progressively dehydrated and malnourished. Due to the combination of aging and continued stressing, the discs begin to degenerate. With continued degeneration, or an excessive stressing event, or both, the annulus fibrosus of a disc may tear, forming one or more fissures (also referred to as fractures). Such fissures may progress to larger tears, which allow the gelatinous material of the nucleus pulposus to flow out of the nucleus and into the outer aspects of the annulus. The flow of the nucleus pulposus to the outer aspects of the annulus may cause a localized bulge or herniation.

When herniation of the nucleus/annulus occurs in the posterior portions of the disc, nerve roots may be directly and physically impinged by the bulge. In more extreme or progressed instances of annular tears, the nuclear material may escape, additionally causing chemical irritation of the nerve roots. Dependent upon the cause and nature of the disc protrusion, the condition may be referred to as a disc stenosis, a disc bulge, a herniated disc, a prolapsed disc, a ruptured disc, or, if the protrusion separates from the disc, a sequestered disc.

Dehydration and progressive degeneration of a disc also leads to thinning of the disc. As the thickness of the disc reduces, the intervertebral foraminae become narrow. Because the nerve roots pass through the intervertebral foraminae, such narrowing may mechanically entrap the nerve roots. This entrapment can cause direct mechanical compression or it may tether the roots, causing excessive tension to the roots during body movement.

Nerve root impingement most often occurs in the lumbar region of the spinal column since the lumbar discs bear significant vertical loads relative to discs in other regions of the spine. In addition, disc protrusions in the lumbar region typically occur posteriorly because the annulus fibrosus is radially thinner on the posterior side than on the anterior side and because normal posture places more compression on the posterior side. Posterior protrusions are particularly problematic since the nerve roots are posteriorly positioned relative to the intervertebral discs. Lower back pain due to nerve root irritation not only results in strong pain in the region of the back adjacent the disc, but may also cause sciatica, or pain radiating down one or both legs. Such pain may also be aggravated by such subtle movements as coughing, bending over, or remaining in a sitting position for an extended period of time.

Another suspected source of disc related back pain is damage and irritation to the small nerve endings which lie in close proximity to or just within the outer aspects of the annulus of the discs. Again, as the disc degenerates and is subjected to stressing events, the annulus fibrosus may be damaged and form fissures. While these fissures can lead to pain via the mechanisms described above, they may also lead to pain emanating from the small nerve endings in or near the annulus, due to mechanical or chemical irritation at the sites of the fissures. The fissures may continue to irritate the small nerve endings, as their presence causes the disc to become structurally weaker, allowing for more localized straining around the fissures. This results in more relative motion of edges of the fissures, increasing mechanical irritation. Because it is believed that these fissures have only limited healing ability once formed, such irritation may only become progressively worse.

A common treatment for a disc herniation is a discectomy, a procedure wherein the protruding portion of the degenerated disc is surgically removed. However, discectomy procedures have an inherent risk since the portion of the disc to be removed is immediately adjacent the nerve root, and any damage to the nerve root is clearly undesirable. Furthermore, discectomy procedures are not always successful long term because scar tissue may form and/or additional disc material may subsequently protrude or reherniate from the disc space as the disc deteriorates further. The recurrence of a disc herniation may necessitate a repeat discectomy procedure, along with its inherent clinical risks and less than perfect long term success rate. Thus, a discectomy procedure, at least as a stand-alone procedure, is clearly not an optimal solution.

Discectomy is also not a viable solution for DDD when no disc/nuclear herniation is involved. As mentioned above, DDD causes the entire disc to degenerate, narrowing the intervertebral space and shifting the load to the facet joints. If the facet joints carry a substantial load, the joints may degrade over time and be a different cause of back pain. Furthermore, the narrowed disc space can result in the intervertebral foramina surrounding the nerve roots directly impinging on one or more nerve roots. Such nerve impingement is very painful and cannot be corrected by a discectomy procedure. Furthermore, a discectomy does not address pain caused by annular fissures or post-surgical defects, which may cause direct mechanical irritation to the small nerve endings near or just within the outer aspect of the annulus of a damaged disc.

As a result of the limitations of a discetomy, spinal fusion, particularly with the assistance of interbody fusion cages, has become a preferred secondary procedure, and in some instances, a preferred primary procedure. Spinal fusion involves permanently fusing or fixing adjacent vertebrae. Hardware in the form of bars, plates, screws, and cages may be utilized in combination with bone graft material to fuse adjacent vertebrae. Spinal fusion may be performed as a stand-alone procedure, or it may be performed in combination with a discectomy procedure. By placement of the adjacent vertebrae in their normal position and fixing them in place, relative movement therebetween may be significantly reduced and the disc space may be restored to its normal condition. Thus, theoretically, aggravation caused by relative movement between adjacent vertebrae may be reduced if not eliminated.

The success rate of spinal fusion procedures is certainly less than perfect for a number of different reasons, none of which are well understood. In addition, even if spinal fusion procedures are initially successful, they may cause accelerated degeneration of adjacent discs since the adjacent discs must accommodate a greater degree of motion. The degeneration of adjacent discs simply leads to the same problem at a different anatomical location, which is clearly not an optimal solution. Furthermore, spinal fusion procedures are invasive to the disc, risk nerve damage, and, dependent upon the procedural approach, are technically complicated (endoscopic anterior approach), invasive to the bowel (surgical anterior approach), and/or invasive to the musculature of the back (surgical posterior approach).

Another procedure that has been less than clinically successful is total disc replacement with a prosthetic disc. This procedure is also very invasive to the disc, and, dependent upon the procedural approach, either invasive to the bowel (surgical anterior approach) or invasive to the musculature of the back (surgical posterior approach). In addition, the procedure may actually complicate matters by creating instability in the spine, and the long-term mechanical reliability of prosthetic discs has yet to be demonstrated.

Many other medical procedures have been proposed to solve the problems associated with degenerative discs or disc protrusions. However, many of the proposed procedures have not been clinically proven, and some of the allegedly beneficial procedures have controversial clinical data. There is a substantial need for improvements in the treatment of spinal disorders, particularly in the treatment of disc related pain associated with a damaged or otherwise unhealthy disc, specifically the repair of disc defects or annulo-nucleoplasty regeneration.

OBJECTS OF THE INVENTION

It is an object of the invention to provide a method for the repair of spinal annular defects.

It is also an object of the invention to provide a composition for the repair of spinal annular defects.

It is a further object of the invention to provide a method and composition for annulo-nucleoplasty regeneration.

It is a yet further object of the invention to provide a method of repairing spinal annular defects where a polymeric or metallic substantially cylindrical member is inserted into the spinal annulus.

It is a yet further object of the invention where a polymeric or metallic substantially cylindrical member is inserted into the spinal annulus to promote annulo-nucleoplasty regeneration.

These and other objects of the invention will become more apparent from the discussion below.

SUMMARY OF THE INVENTION

The invention described and claimed below relates to the repair of spinal annular defects. According to the invention, a substantially cylindrical member is inserted through an opening in the spinal annulus to the extent that the distal portion of the substantially cylindrical member extends into the spinal nuclear defect. The substantially cylindrical member is comprised of a biodurable reticulated compressible material that expands to seal the opening. Optionally the cylindrical member can comprise one or more metal components that open after insertion to assist in maintaining the sealing ability of the substantially cylindrical member.

The present invention addresses this need by providing improved devices and methods for the treatment of spinal disorders. The improved devices and methods of the present invention specifically address disc related pain, progressive disc degeneration, and/or reherniation of nuclear material, particularly in the lumbar region, but may have other significant applications not specifically mentioned herein. For purposes of illustration only, and without limitation, the present invention is discussed in detail with reference to the treatment of damaged discs in the lumbar region of the adult human spinal column.

As will become apparent from the following detailed description, the improved devices and methods of the present invention reduce if not eliminate back pain while maintaining near normal anatomical motion. Specifically, the present invention provides an annular repair and/or annulo-nucleoplasty regeneration mechanism, while permitting relative movement of the vertebrae adjacent the damaged disc. The devices of the present invention are particularly well suited for minimally invasive methods of implantation.

The devices of the present invention provide three distinct functions. First, the reinforcement devices mechanically stabilize and strengthen the annular portion of the spinal disc to minimize, if not eliminate, chronic irritation of local nerve roots and nerve endings adjacent to the periphery of the disc annulus. Second, the devices radially and/or circumferentially conform to the surgical and/or pathologic present fissures, fractures, and tears of the disc, thereby preventing the prolapse of extra spinal disc tissue such as nerves and muscle, thereby potentially facilitating healing. And third, the devices may be used to stabilize the nuclear portion of the disc after a discectomy procedure to reduce the need for a subsequent operation or treatment due to reherniation.

In an exemplary embodiment, the present invention provides disc reinforcement in which a device of the invention is implanted into the annulus of an intervertebral disc. The implantation method may be performed by a percutaneous procedure or by a minimally invasive surgical procedure. The present invention provides a number or tools to facilitate percutaneous implantation. One or more reinforcement members may be implanted, for example, posteriorly, anteriorly, and/or laterally, and may be oriented circumferentially or radially. As such, the reinforcement members may be used to stabilize the annulus and/or a portion of the annulus so as to reduce recurrent bulges and/or obliterate annular tracts.

The implant device may be sized to pass through a trocar and/or may have a tubular cross-section to facilitate advancement over a stylet. The implant device preferably includes a body portion sized to fit in an opening in the annulus and as an anchor for engaging the annulus and limiting relative movement therebetween. The anchor may be disposed only at the distal portions of the implant body, or may extend over the entire length of the body. The anchor may comprise threads which may have a variable pitch to facilitate compression of the annulus during implantation. The implant device may incorporate chemical and/or biological agents. The implant device may comprise a biocompatible metal such as stainless steel or a super elastic (nickel titanium) alloy. Alternatively, the implant device may comprise a polymer or a reinforced polymeric structure. As a further alternative, the implant device may comprise a bioabsorbable material.

DETAILED DESCRIPTION OF THE INVENTION

Figure 1:
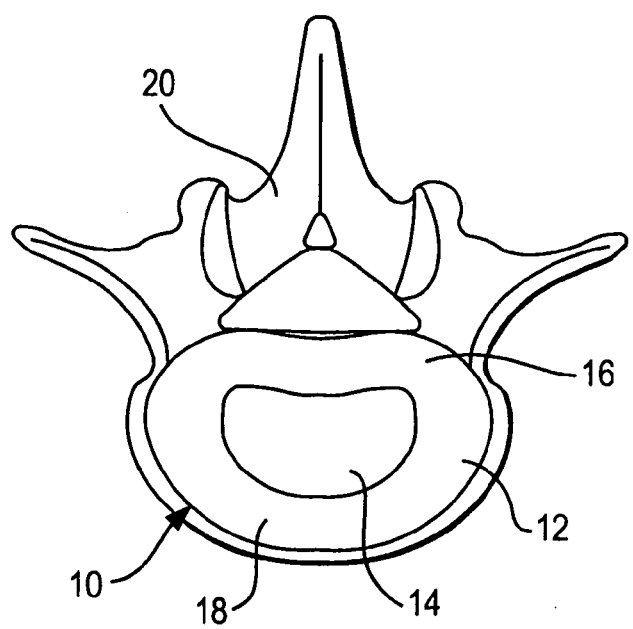
FIG. 1 illustrate a superior (top) view of a healthy disc.

The invention can perhaps be better appreciated from the drawings. FIG. 1 is a simplified representation of a spinal disc 10 that comprises an annulus fibrosis or annulus 12 surrounding a nucleus pulposus or nucleus 14. The posterior annulus 16 is generally thinner than the anterior annulus 18, which may account for the higher incidence of posterior disc protrusions.

A common theory is that each intervertebral disc 10 forms one support point and the facet joints of the spinal column (not shown) form two support points of what may be characterized as a three point support structure between adjacent vertebrae 20. However, in the lumbar region, the facet joints are substantially vertical, leaving the disc 10 to carry the vast majority of the load. As between the annulus 12 and the nucleus 14 of the disc 10, it is commonly believed that the nucleus 14 bears the majority of the load. This belief is based on the theory that the disc 10 behaves much like a balloon or tire, wherein the annulus 12 merely serves to contain the pressurized nucleus 14, and the nucleus 14 bears all the load. However, this theory is questionable since the annulus 12 comprises 60% of the total disc 10 cross-sectional area and is made of 40-60% organized collagen in the form of a laminated structure. By contrast, the nucleus 14 only comprises 40% of the total disc 10 cross-section and is made of 18-30% collagen in the form of a relatively homogenous gel. Thus, a more plausible theory is that the annulus 12 is the primary load bearing portion of the disc 10.

Figure 2:
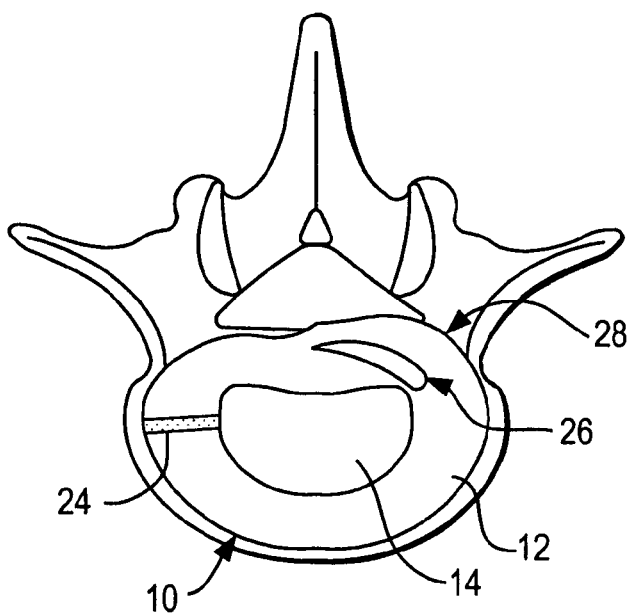
FIGS. 2 and 3 each illustrate a superior (top) view of a degenerated disc.
Figure 3:
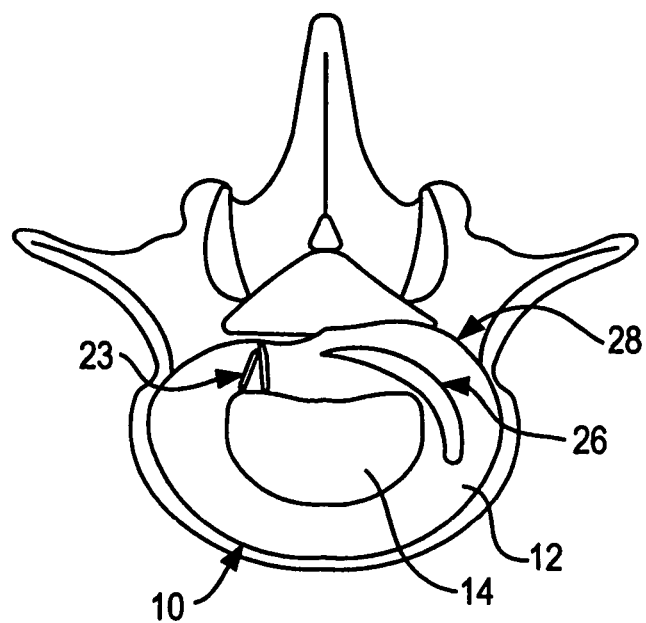

The intervertebral disc 10 becomes progressively dehydrated and malnourished with age, as shown in FIGS. 2 and 3. In combination with continued stressing, the disc begins to degenerate. With continued degeneration, or an excessive stressing event, the annulus of the disc may tear, forming one or more radial fissures 23 or tracts 24 or circumferential fissures 26, which may progress to larger tears. Larger tears may allow the gelatinous material of the nucleus pulposus 14 to flow out of the nucleus through a fissure 24 and into the outer aspects of the annulus 12. Nuclear material that escapes through an advanced tear may cause further mechanical irritation and additionally cause chemical irritation of a nerve root.

The flow of the nucleus 14 to the outer aspects of the annulus 12 may cause a localized bulge 28. A posterior bulge 28 may result in direct impingement of a nerve root (not shown).

A nerve root may also be compressed or tethered by a narrowing of the intervertebral foraminae, resulting from a loss in disc height caused by sustained degeneration of the disc 10. Small nerve endings (not shown) in or near the perimeter of the annulus 12 may also be mechanically or chemically irritated at the sites of the fissures 24, 26. In all cases, degeneration of the disc eventually leads to disc related pain of some origin.

Figure 4:
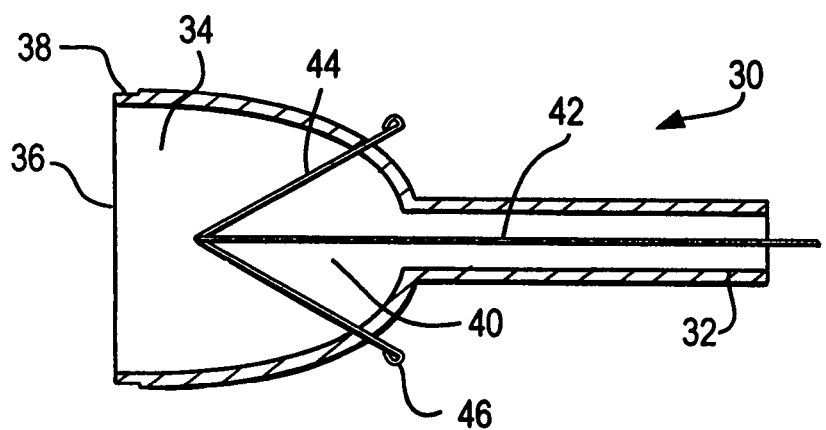
FIG. 4 is a partially cross-sectional view of an embodiment of a substantially cylindrical member according to the invention.

In an embodiment of the invention shown in FIG. 4, a partially cylindrical device 30 comprises a cylindrical portion 32 and an attached expanded, at least partially spherical portion 34. Portion 34 may be entirely spherical or it may optionally have a substantially flat surface 36 bordered by edge 38. Portions 32 and 34 are both solid, although optionally each may contain a longitudinal lumen (not shown) to facilitate threading member 30 over a wire or stylet (not shown). Also, device 30 may optionally contain a retainer 40, comprising a longitudinal member 42 and collapsible/expandable members 44. Preferably the proximal end of each member 44 has a tissue fixation member 46 that contacts the inner portion of the annulus when members 44 expand, to hold or fix device 30 in position. Retainer 40 preferably is comprised of a physiologically acceptable metal such as nitinol or stainless steel and, after compression, expands to form an umbrella-like shape.

Figure 5:
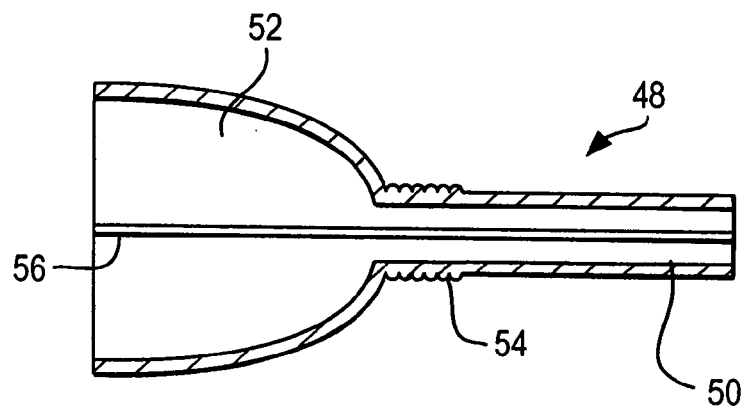
FIG. 5 is a partially cross-sectional view of an embodiment of an at least partially cylindrical member according to the invention.

In the embodiment of the invention shown in FIG. 5, a partially cylindrical device 48 comprises a cylindrical portion 50 and a goblet- or mushroom-shaped distal portion 52. Preferably cylindrical portion 50 has ridges or projections 54 that aid in fixating device 48 in an annular fissure, especially at the inner portion of the fissure. Optionally device 48 has a lumen 56 to facilitate positioning device 48 over a stylet or wire (not shown).

Figure 6:
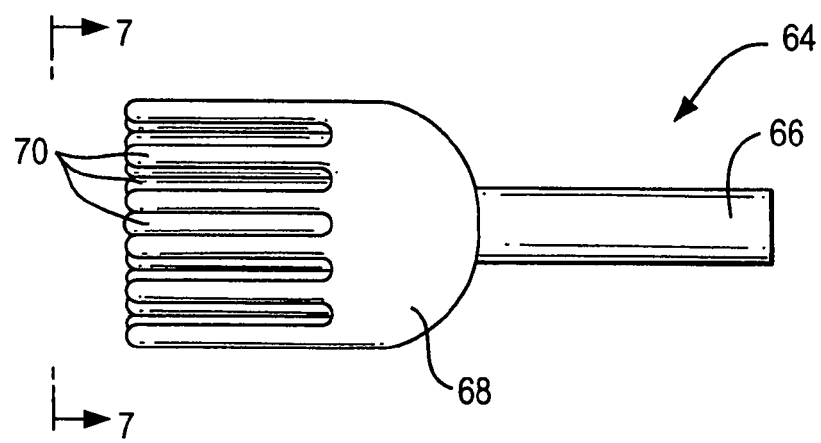
FIG. 6 is a partially cross-sectional view of a further embodiment of another at least partially cylindrical member according to the invention.
Figure 7:
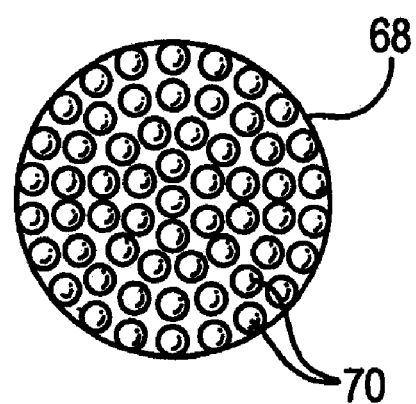
FIG. 7 is a cross-sectional view across the line 7-7 of the embodiment of the invention shown in FIG. 6

The embodiment of the invention shown in FIGS. 6 and 7 is an at least partially cylindrical member 64 that comprises a cylindrical member 66 and a distal semispherical portion 68 that comprises distally extending projections 70. Preferably projections 70 comprise spaghetti-like shapes suitable for cell propagation.

The device of the invention comprises a biodurable, compressible elastomeric, reticulated scaffold or matrix that can be compressed for insertion and then expands in place. The scaffold can be comprised of any known or to be formulated material that is suitable for the application described herein.

A scaffold useful in the implantable device of the invention is reticulated, i.e., it comprises an interconnected network of pores, either by being formed having a reticulated structure and/or undergoing a reticulation process. This provides fluid permeability throughout the implantable device and permits cellular ingrowth and proliferation into the interior of the implantable device. For this purpose, in one embodiment, the reticulated elastomeric matrix has pores with an average diameter or other largest transverse dimension of at least about 20 μm. In another embodiment, the reticulated elastomeric matrix has pores with an average diameter or other largest transverse dimension of from about 20 μm to about 500 μm. In a further embodiment, the reticulated elastomeric matrix has pores with an average diameter or other largest transverse dimension of from about 80 μm to about 100 μm.

According to the invention, an implantable device comprise a reticulated elastomeric matrix that is flexible and resilient and can recover its shape and most of its size after compression. In one embodiment, the inventive implantable devices have a resilient compressibility that allows the implantable device to be compressed under ambient conditions, e.g., at 25° C., from a relaxed configuration to a first, compact configuration for in vivo delivery via a delivery-device and to expand to a second, working configuration, in situ. In one embodiment, elastomeric matrices of the invention have sufficient resilience to allow substantial recovery, e.g., to at least about 50% of the size of the relaxed configuration in at least one dimension, after being compressed for implantation in the human body, for example, a low compression set, e.g., at 25° C. or 37° C., and sufficient strength and flow-through for the matrix to be used for controlled release of pharmaceutically-active agents, such as a drug, and for other medical applications. In another embodiment, elastomeric matrices of the invention have sufficient resilience to allow recovery to at least about 60% of the size of the relaxed configuration in at least one dimension after being compressed for implantation in the human body. In another embodiment, elastomeric matrices of the invention have sufficient resilience to allow recovery to at least about 90% of the size of the relaxed configuration in at least one dimension after being compressed for implantation in the human body.

The present invention can provide truly reticulated, flexible, resilient, biodurable elastomeric matrix, suitable for long-term implantation and having sufficient porosity to encourage cellular ingrowth and proliferation, in vivo.

In one embodiment of the invention, a biodurable reticulated elastomeric matrix has a coating comprising material selected to encourage cellular ingrowth and proliferation. The coating material can, for example, comprise a foamed coating of a biodegradable material, optionally, collagen, fibronectin, elastin, hyaluronic acid and mixtures thereof. Alternatively, the coating comprises a biodegradable polymer and an inorganic component.

In another embodiment, the reticulated biodurable elastomer is coated or impregnated with a material such as, for example, polyglycolic acid ("PGA"), polylactic acid ("PLA"), polycaprolactic acid ("PCL"), poly-p-dioxanone ("PDO"), PGA/PLA copolymers, PGA/PCL copolymers, PGA/PDO copolymers, PLA/PCL copolymers, PLA/PDO copolymers, PCL/PDO copolymers or combinations of any two or more of the foregoing.

In one embodiment, the invention comprises an implantable device having sufficient resilient compressibility to be delivered by a "delivery-device", i.e., a device with a chamber for containing an elastomeric implantable device while it is delivered to the desired site then released at the site, e.g., using a trocar, cannula, or catheter with assistant visualization through an endoscopic instrument such as an arthroscope, laproscope, or cystoscope. In another embodiment, the thus-delivered elastomeric implantable device substantially regains its shape after delivery to a biological site and has adequate biodurability and biocompatibility characteristics to be suitable for long-term implantation.

The structure, morphology and properties of the elastomeric matrices of this invention can be engineered or tailored over a wide range of performance by varying the starting materials and/or the processing conditions for different functional or therapeutic uses.

In the present application, the term "biodurable" describes elastomers and other products that are stable for extended periods of time in a biological environment. Such products should not exhibit significant symptoms of breakdown or degradation, erosion or significant deterioration of mechanical properties relevant to their employment when exposed to biological environments for periods of time commensurate with the use of the implantable device. The biodurable products of the invention are also biocompatible, that is, they induce few, if any, adverse biological reactions when implanted in a host patient.

Preferred structural materials for the inventive porous elastomers are synthetic polymers, especially, but not exclusively, elastomeric polymers that are resistant to biological degradation, for example, polycarbonate polyurethanes, polyether polyurethanes, polysiloxanes and the like. Such elastomers are generally hydrophobic but, pursuant to the invention, may be treated to have surfaces that are less hydrophobic or somewhat hydrophilic. In another embodiment, such elastomers may be produced with surfaces that are less hydrophobic or somewhat hydrophilic.

In one embodiment, the reticulated elastomeric matrix has sufficient structural integrity to be self-supporting and free-standing in vitro. However, in another embodiment, the elastomeric matrix can be furnished with structural supports such as ribs or struts.

The reticulated elastomeric matrix useful according to the invention should have sufficient tensile strength such that it can withstand normal manual or mechanical handling during its intended application and during post-processing steps that may be required or desired without tearing, breaking, crumbling, fragmenting or otherwise disintegrating, shedding pieces or particles, or otherwise losing its structural integrity. The tensile strength of the starting material(s) should not be so high as to interfere with the fabrication or other processing of the elastomeric matrix.

In a preferred embodiment of the invention, a biodurable elastomeric polyurethane matrix comprises a polymerization reaction product of a polycarbonate polyol component and an isocyanate component, involving crosslinking and foaming, thereby forming pores, followed by reticulation of the foam to provide a reticulated product. The product is designated as a polycarbonate polyurethane, being a polymer comprising urethane groups formed from, e.g., the hydroxyl groups of the polycarbonate polyol component and the isocyanate groups of the isocyanate component. The process employs controlled chemistry to provide a reticulated elastomer product with good biodurability characteristics, and the polymerization is conducted to provide a foam product employing chemistry that avoids biologically undesirable or nocuous constituents therein.

In one embodiment, as one starting material, the process employs at least one polyol component, where the term "polyol component" includes molecules comprising, on the average, about 2 hydroxyl groups per molecule, i.e., a difunctional polyol or a diol, as well as those molecules comprising, on the average, greater than about 2 hydroxyl groups per molecule, i.e., a polyol or a multi-functional polyol. Exemplary polyols can comprise, on the average, from about 2 to about 5 hydroxyl groups per molecule. In one embodiment, as one starting material, the process employs a difunctional polyol component. In this embodiment, because the hydroxyl group functionality of the diol is about 2, it does not provide the so-called "soft segment" with soft segment crosslinking. In another embodiment, as one starting material of the polyol component, the process employs a multi-functional polyol component in sufficient quantity to provide a controlled degree of soft segment crosslinking. In another embodiment, the process provides sufficient soft segment crosslinking to yield a stable foam. In another embodiment, the soft segment is composed of a polyol component that is generally of a relatively low molecular weight, typically from about 1,000 to about 6,000 Daltons. Thus, these polyols are generally liquids or low-melting-point solids. This soft segment polyol is terminated with hydroxyl groups, either primary or secondary. In another embodiment, a soft segment polyol component has about 2 hydroxyl groups per molecule. In another embodiment, a soft segment polyol component has greater than about 2 hydroxyl groups per molecule; more than 2 hydroxyl groups per polyol molecule are required of some polyol molecules to impart soft-segment crosslinking.

In one embodiment, the average number of hydroxyl groups per molecule in the polyol component is about 2. In another embodiment, the average number of hydroxyl groups per molecule in the polyol component is greater than about 2. In another embodiment, the average number of hydroxyl groups per molecule in the polyol component is greater than 2. In one embodiment, the polyol component comprises a tertiary carbon linkage. In one embodiment, the polyol component comprises a plurality of tertiary carbon linkages. The polyol component can be, for example, a polyether polyol, polyester polyol, polycarbonate polyol, hydrocarbon polyol, polysiloxane polyol, poly(ether-co-ester) polyol, poly(ether-co-carbonate) polyol, poly(ether-co-hydrocarbon) polyol, poly(ether-co-siloxane) polyol, poly(ester-co-carbonate) polyol, poly(ester-co-hydrocarbon) polyol, poly(ester-co-siloxane) polyol, poly(carbonate-co-hydrocarbon) polyol, poly(carbonate-co-siloxane) polyol, poly(hydrocarbon-co-siloxane) polyol, or mixtures thereof.

Polyether-type polyols are oligomers of, e.g., alkylene oxides such as ethylene oxide or propylene oxide, polymerized with glycols or polyhydric alcohols, the latter to result in hydroxyl functionalities greater than 2 to allow for soft segment crosslinking. Polyester-type polyols are oligomers of, e.g., the reaction product of a carboxylic acid with a glycol or triol, such as ethylene glycol adipate, propylene glycol adipate, butylene glycol adipate, diethylene glycol adipate, phthalates, polycaprolactone and castor oil. When the reactants include those with hydroxyl functionalities greater than 2, e.g., polyhydric alcohols, soft segment crosslinking is possible.

Polycarbonate-type polyols typically result from the reaction, with a carbonate monomer, of one type of hydrocarbon diol or, for a plurality of diols, hydrocarbon diols each with a different hydrocarbon chain length between the hydroxyl groups. The length of the hydrocarbon chain between adjacent carbonates is the same as the hydrocarbon chain length of the original diol(s). For example, a difunctional polycarbonate polyol can be made by reacting 1,6-hexanediol with a carbonate, such as sodium hydrogen carbonate, to provide the polycarbonate-type polyol 1,6-hexanediol carbonate. The molecular weight for the commercial-available products of this reaction varies from about 1,000 to about 5,000 Daltons. If the polycarbonate polyol is a solid at 25° C., it is typically melted prior to further processing. Alternatively, in one embodiment, a liquid polycarbonate polyol component can prepared from a mixture of hydrocarbon diols, e.g., all three or any binary combination of 1,6-hexanediol, cyclohexyl dimethanol and 1,4-butanediol. Without being bound by any particular theory, such a mixture of hydrocarbon diols is thought to break-up the crystallinity of the product polycarbonate polyol component, rendering it a liquid at 25° C., and thereby, in foams comprising it, yield a relatively softer foam.

When the reactants used to produce the polycarbonate polyol include those with hydroxyl functionalities greater than 2, e.g., polyhydric alcohols, soft segment crosslinking is possible. Polycarbonate polyols with an average number of hydroxyl groups per molecule greater than 2, e.g., a polycarbonate triol, can be made by using, for example, hexane triol, in the preparation of the polycarbonate polyol component. To make a liquid polycarbonate triol component, mixtures with other hydroxyl-comprising materials, for example, cyclohexyl trimethanol and/or butanetriol, can be reacted with the carbonate along with the hexane triol.

Commercial hydrocarbon-type polyols typically result from the free-radical polymerization of dienes with vinyl monomers, therefore, they are typically difunctional hydroxyl-terminated materials.

Polysiloxane polyols are oligomers of, e.g., alkyl and/or aryl substituted siloxanes such as dimethyl siloxane, diphenyl siloxane or methyl phenyl siloxane, comprising hydroxyl end-groups. Polysiloxane polyols with an average number of hydroxyl groups per molecule greater than 2, e.g., a polysiloxane triol, can be made by using, for example, methyl hydroxymethyl siloxane, in the preparation of the polysiloxane polyol component.

A particular type of polyol need not, of course, be limited to those formed from a single monomeric unit. For example, a polyether-type polyol can be formed from a mixture of ethylene oxide and propylene oxide.

Additionally, in another embodiment, copolymers or copolyols can be formed from any of the above polyols by methods known to those in the art. Thus, the following binary component polyol copolymers can be used: poly(ether-co-ester) polyol, poly(ether-co-carbonate) polyol, poly(ether-co-hydrocarbon) polyol, poly(ether-co-siloxane) polyol, poly(ester-co-carbonate) polyol, poly(ester-co-hydrocarbon) polyol, poly(ester-co-siloxane) polyol, poly(carbonate-co-hydrocarbon) polyol, poly(carbonate-co-siloxane) polyol and poly(hydrocarbon-co-siloxane) polyol. For example, a poly(ether-co-ester) polyol can be formed from units of polyethers formed from ethylene oxide copolymerized with units of polyester comprising ethylene glycol adipate. In another embodiment, the copolymer is a poly(ether-co-carbonate) polyol, poly(ether-co-hydrocarbon) polyol, poly(ether-co-siloxane) polyol, poly(carbonate-co-hydrocarbon) polyol, poly(carbonate-co-siloxane) polyol, poly(hydrocarbon-co-siloxane) polyol or mixtures thereof. In another embodiment, the copolymer is a poly(carbonate-co-hydrocarbon) polyol, poly(carbonate-co-siloxane) polyol, poly(hydrocarbon-co-siloxane) polyol or mixtures thereof. In another embodiment, the copolymer is a poly(carbonate-co-hydrocarbon) polyol. For example, a poly(carbonate-co-hydrocarbon) polyol can be formed by polymerizing 1,6-hexanediol, 1,4-butanediol and a hydrocarbon-type polyol with carbonate.

In another embodiment, the polyol component is a polyether polyol, polycarbonate polyol, hydrocarbon polyol, polysiloxane polyol, poly(ether-co-carbonate) polyol, poly(ether-co-hydrocarbon) polyol, poly(ether-co-siloxane) polyol, poly(carbonate-co-hydrocarbon) polyol, poly(carbonate-co-siloxane) polyol, poly(hydrocarbon-co-siloxane) polyol or mixtures thereof. In another embodiment, the polyol component is a polycarbonate polyol, hydrocarbon polyol, polysiloxane polyol, poly(carbonate-co-hydrocarbon) polyol, poly(carbonate-co-siloxane) polyol, poly(hydrocarbon-co-siloxane) polyol or mixtures thereof. In another embodiment, the polyol component is a polycarbonate polyol, poly(carbonate-co-hydrocarbon) polyol, poly(carbonate-co-siloxane) polyol, poly(hydrocarbon-co-siloxane) polyol or mixtures thereof. In another embodiment, the polyol component is a polycarbonate polyol, poly(carbonate-co-hydrocarbon) polyol, poly(carbonate-co-siloxane) polyol or mixtures thereof. In another embodiment, the polyol component is a polycarbonate polyol.

Furthermore, in another embodiment, mixtures, admixtures and/or blends of polyols and copolyols can be used in the elastomeric matrix of the present invention. In another embodiment, the molecular weight of the polyol is varied. In another embodiment, the functionality of the polyol is varied.

In another embodiment, as either difunctional polycarbonate polyols or difunctional hydrocarbon polyols cannot, on their own, induce soft segment crosslinking, higher functionality is introduced into the formulation through the use of a chain extender component with a hydroxyl group functionality greater than about 2. In another embodiment, higher functionality is introduced through the use of an isocyanate component with an isocyanate group functionality greater than about 2.

Commercial polycarbonate diols with molecular weights of from about 2,000 to about 6,000 Daltons are available from Stahl, Inc. (Netherlands) and Bayer Corp. (Leverkusen, Germany). Commercial hydrocarbon polyols are available from Sartomer (Exton, Pa.). Commercial polyether polyols are readily available, such as the PLURACOL®, e.g., PLURACOL® GP430 with functionality of 3 and LUPRANOL® lines from BASF Corp. (Wyandotte, Mich.), VORANOL® from Dow Chemical Corp. (Midland, Mich.), BAYCOLL® B, DESMOPHEN® and MULTRANOL® from Bayer, and from Huntsman Corp. (Madison Heights, Mich.). Commercial polyester polyols are readily available, such as LUPRAPHEN® from BASF, TONE® polycaprolactone and VORANOL from Dow, BAYCOLL A and the DESMOPHEN® U series from Bayer, and from Huntsman. Commercial polysiloxane polyols are readily available, such as from Dow.

The preparation process also employs at least one isocyanate component and, optionally, at least one chain extender component to provide the so-called "hard segment". For the purposes of this application, the term "isocyanate component" includes molecules comprising, on the average, about 2 isocyanate groups per molecule as well as those molecules comprising, on the average, greater than about 2 isocyanate groups per molecule. The isocyanate groups of the isocyanate component are reactive with reactive hydrogen groups of the other ingredients, e.g., with hydrogen bonded to oxygen in hydroxyl groups and with hydrogen bonded to nitrogen in amine groups of the polyol component, chain extender, crosslinker and/or water.

In one embodiment, the average number of isocyanate groups per molecule in the isocyanate component is about 2. In another embodiment, the average number of isocyanate groups per molecule in the isocyanate component is greater than about 2. In another embodiment, the average number of isocyanate groups per molecule in the isocyanate component is greater than 2.

The isocyanate index, a quantity well known to those in the art, is the mole ratio of the number of isocyanate groups in a formulation available for reaction to the number of groups in the formulation that are able to react with those isocyanate groups, e.g., the reactive groups of diol(s), polyol component(s), chain extender(s) and water, when present. In one embodiment, the isocyanate index is from about 0.9 to about 1.1. In another embodiment, the isocyanate index is from about 0.9 to about 1.02. In another embodiment, the isocyanate index is from about 0.98 to about 1.02. In another embodiment, the isocyanate index is from about 0.9 to about 1.0. In another embodiment, the isocyanate index is from about 0.9 to about 0.98.

Exemplary diisocyanates include aliphatic diisocyanates, isocyanates comprising aromatic groups, the so-called "aromatic diisocyanates", and mixtures thereof. Aliphatic diisocyanates include tetramethylene diisocyanate, cyclohexane-1,2-diisocyanate, cyclohexane-1,4-diisocyanate, hexamethylene diisocyanate, isophorone diisocyanate, methylene-bis-(p-cyclohexyl isocyanate) ("$H_{12}$ MDI"), and mixtures thereof. Aromatic diisocyanates include p-phenylene diisocyanate, 4,4'-diphenylmethane diisocyanate ("4,4'-MDI"), 2,4'-diphenylmethane diisocyanate ("2,4'-MDI"), 2,4-toluene diisocyanate ("2,4-TDI"), 2,6-toluene diisocyanate ("2,6-TDI"), m-tetramethylxylene diisocyanate, and mixtures thereof.

Exemplary isocyanate components comprising, on the average, greater than about 2 isocyanate groups per molecule, include an adduct of hexamethylene diisocyanate and water comprising about 3 isocyanate groups, available commercially as DESMODUR® N100 from Bayer, and a trimer of hexamethylene diisocyanate comprising about 3 isocyanate groups, available commercially as MONDUR® N3390 from Bayer.

In one embodiment, the isocyanate component contains a mixture of at least about 5% by weight of 2,4'-MDI with the balance 4,4'-MDI. In another embodiment, the isocyanate component contains a mixture of at least 5% by weight of 2,4'-MDI with the balance 4,4'-MDI. In another embodiment, the isocyanate component contains a mixture of from about 5% to about 50% by weight of 2,4'-MDI with the balance 4,4'-MDI. In another embodiment, the isocyanate component contains a mixture of from 5% to about 50% by weight of 2,4'-MDI with the balance 4,4'-MDI. In another embodiment, the isocyanate component contains a mixture of from about 5% to about 40% by weight of 2,4'-MDI with the balance 4,4'-MDI. In another embodiment, the isocyanate component contains a mixture of from 5% to about 40% by weight of 2,4'-MDI with the balance 4,4'-MDI. In another embodiment, the isocyanate component contains a mixture of from 5% to about 35% by weight of 2,4'-MDI with the balance 4,4'-MDI. Without being bound by any particular theory, it is thought that the use of higher amounts of 2,4'-MDI in a blend with 4,4'-MDI results in a softer elastomeric matrix because of the disruption of the crystallinity of the hard segment arising out of the asymmetric 2,4'-MDI structure.

Suitable diisocyanates include MDI, such as ISONATE® 125M, certain members of the PAPI® series from Dow and MONDUR M from Bayer; TDI, e.g., from Lyondell Corp. (Houston, Tex.); isophorone diisocyanate, such as VESTAMAT® from Degussa (Germany); $H_{12}$ MDI, such as DESMODUR W from Bayer; and various diisocyanates from BASF.

Suitable isocyanate components comprising, on the average, greater than about 2 isocyanate groups per molecule, include the following modified diphenylmethane-diisocyanate type, each available from Dow: ISOBIND® 1088, with an isocyanate group functionality of about 3; ISONATE 143L, with an isocyanate group functionality of about 2.1; PAPI 27, with an isocyanate group functionality of about 2.7; PAPI 94, with an isocyanate group functionality of about 2.3; PAPI 580N, with an isocyanate group functionality of about 3; and PAPI 20, with an isocyanate group functionality of about 3.2.

Exemplary chain extenders include diols, diamines, alkanol amines and mixtures thereof. In one embodiment, the chain extender is an aliphatic diol having from 2 to 10 carbon atoms. In another embodiment, the diol chain extender is selected from ethylene glycol, 1,2-propane diol, 1,3-propane diol, 1,4-butane diol, 1,5-pentane diol, diethylene glycol, triethylene glycol and mixtures thereof. In another embodiment, the chain extender is a diamine having from 2 to 10 carbon atoms. In another embodiment, the diamine chain extender is selected from ethylene diamine, 1,3-diaminobutane, 1,4-diaminobutane, 1,5 diaminopentane, 1,6-diaminohexane, 1,7-diaminoheptane, 1,8-diaminooctane, isophorone diamine and mixtures thereof. In another embodiment, the chain extender is an alkanol amine having from 2 to 10 carbon atoms. In another embodiment, the alkanol amine chain extender is selected from diethanolamine, triethanolamine, isopropanolamine, dimethylethanolamine, methyldiethanolamine, diethylethanolamine and mixtures thereof.

Commercially available chain extenders include the JEFFAMINE® series of diamines, triamines and polyetheramines available from Huntsman, VERSAMIN® isophorone diamine from Creanova, the VERSALINK® series of diamines available from Air Products Corp. (Allentown, Pa.), ethanolamine, diethylethanolamine and isopropanolamine available from Dow, and various chain extenders from Bayer, BASF and UOP Corp. (Des Plaines, Ill.).

In one embodiment, a small quantity of an optional ingredient, such as a multi-functional hydroxyl compound or other crosslinker having a functionality greater than 2, e.g., glycerol, is present to allow crosslinking. In another embodiment, the optional multi-functional crosslinker is present in an amount just sufficient to achieve a stable foam, i.e., a foam that does not collapse to become non-foamlike. Alternatively, or in addition, polyfunctional adducts of aliphatic and cycloaliphatic isocyanates can be used to impart crosslinking in combination with aromatic diisocyanates. Alternatively, or in addition, polyfunctional adducts of aliphatic and cycloaliphatic isocyanates can be used to impart crosslinking in combination with aliphatic diisocyanates.

Optionally, the process employs at least one catalyst in certain embodiments selected from a blowing catalyst, e.g., a tertiary amine, a gelling catalyst, e.g., dibutyltin dilaurate, and mixtures thereof. Moreover, it is known in the art that tertiary amine catalysts can also have gelling effects, that is, they can act as a blowing and gelling catalyst. Exemplary tertiary amine catalysts include the TOTYCAT® line from Toyo Soda Co. (Japan), the TEXACAT® line from Texaco Chemical Co. (Austin, Tex.), the KOSMOS® and TEGO® lines from Th. Goldschmidt Co. (Germany), the DMP® line from Rohm and Haas (Philadelphia, Pa.), the KAO LIZER® (line from Kao Corp. (Japan), and the QUINCAT® line from Enterprise Chemical Co. (Altamonte Springs, Fla.). Exemplary organotin catalysts include the FOMREZ® and FOMREZ UL® lines from Witco Corporation (Middlebury, Conn.), the COCURE® and COSCAT® lines from Cosan Chemical Co. (Carlstadt, N.J.), and the DABCO® and POLYCAT® lines from Air Products.

In certain embodiments, additives helpful in achieving a stable foam, for example, surfactants and catalysts, can be included. By limiting the quantities of such additives to the minimum desirable while maintaining the functionality of each additive, the impact on the toxicity of the product can be controlled.

In one embodiment, elastomeric matrices of various densities, e.g., from about 0.005 to about 0.15 g/cc (from about 0.31 to about 9.4 $lb/ft^3$) are produced. The density is controlled by, e.g., the amount of blowing or foaming agent, the isocyanate index, the isocyanate component content in the formulation, the reaction exotherm, and/or the pressure of the foaming environment.

Of particular interest as starting products to prepare reticulated scaffolds are thermoplastic elastomers such as polyurethanes, whose chemistry is associated with good biodurability properties, for example. In one embodiment, such thermoplastic polyurethane elastomers include polycarbonate polyurethanes, polyester polyurethanes, polyether polyurethanes, polysiloxane polyurethanes, polyurethanes with so-called "mixed" soft segments, and mixtures thereof. Mixed soft segment polyurethanes are known to those skilled in the art and include, e.g., polycarbonate-polyester polyurethanes, polycarbonate-polyether polyurethanes, polycarbonate-polysiloxane polyurethanes, polyester-polyether polyurethanes, polyester-polysiloxane polyurethanes and polyether-polysiloxane polyurethanes. In another embodiment, the thermoplastic polyurethane elastomer comprises at least one diisocyanate in the isocyanate component, at least one chain extender and at least one diol, and may be formed from any combination of the diisocyanates, difunctional chain extenders and diols described in detail above.

In one embodiment, the weight average molecular weight of the thermoplastic elastomer is from about 30,000 to about 500,000 Daltons. In another embodiment, the weight average molecular weight of the thermoplastic elastomer is from about 50,000 to about 250,000 Daltons.

Some suitable thermoplastic polyurethanes for practicing the invention, in one embodiment suitably characterized as described herein, include: polyurethanes with mixed soft segments comprising polysiloxane together with a polyether and/or a polycarbonate component, as disclosed by Meijs et al. in U.S. Pat. No. 6,313,254; and those polyurethanes disclosed by DiDomenico et al. in U.S. Pat. Nos. 6,149,678, 6,111,052 and 5,986,034. In another embodiment, an optional therapeutic agent may be loaded into the appropriate block of other elastomers used in the practice of the invention.

Some commercially-available thermoplastic elastomers suitable for further processing to form reticulated scaffolds according to the invention include the line of polycarbonate polyurethanes supplied under the trademark BIONATE® by The Polymer Technology Group Inc. (Berkeley, Calif.). For example, the very well-characterized grades of polycarbonate polyurethane polymer BIONATE® 80A, 55 and 90 are soluble in THF, processable, reportedly have good mechanical properties, lack cytotoxicity, lack mutagenicity, lack carcinogenicity and are non-hemolytic. Another commercially-available elastomer suitable for use in practicing the present invention is the CHRONOFLEX® C line of biodurable medical grade polycarbonate aromatic polyurethane thermoplastic elastomers available from CardioTech International, Inc. (Woburn, Mass.). Yet another commercially-available elastomer suitable for use in practicing the present invention is the PELLETHANE® line of thermoplastic polyurethane elastomers, in particular the 2363 series products and more particularly those products designated 81A and 85A, supplied by The Dow Chemical Company (Midland, Mich.). These commercial polyurethane polymers are linear, not crosslinked, polymers, therefore, they are soluble, readily analyzable and readily characterizable.

Preferred elastomeric materials useful as in the implantable devices of the invention are described above as well as in more detail in co-pending U.S. patent application Ser. No. 60/471,518, filed May 15, 2003, which application is incorporated herein by reference for the description of the elastomeric materials, the preparation thereof, and the further treatment of the elastomeric materials to prepare scaffolds using hot wax and other procedures and to impart additional properties and characteristics to resulting scaffolds.

It is within the scope of this invention that the elastomeric scaffold may optionally have a simple dip or spray polymer coating, the coating optionally comprising a pharmaceutically-active agent, such as a therapeutic agent or drug. In one embodiment the coating may be a solution and the polymer content in the coating solution is from about 1% to about 40% by weight. In another embodiment, the polymer content in the coating solution may be from about 1% to about 20% by weight. In another embodiment, the polymer content in the coating solution may be from about 1% to about 10% by weight.

The solvent or solvent blend for the coating solution is chosen with consideration given to, inter alia, the proper balancing the viscosity, deposition level of the polymer, wetting rate and evaporation rate of the solvent to properly coat solid phase as known to those in the art. In one embodiment, the solvent is chosen such the polymer is soluble in the solvent. In another embodiment, the solvent is substantially completely removed from the coating. In another embodiment, the solvent is non-toxic, non-carcinogenic and environmentally benign. Mixed solvent systems can be advantageous for controlling the viscosity and evaporation rates. In all cases, the solvent should not react with the coating polymer. Solvents include, but are not limited to, acetone, N-methylpyrrolidone ("NMP"), DMSO, toluene, methylene chloride, chloroform, 1,1,2-trichloroethane ("TCE"), various freons, dioxane, ethyl acetate, THF, DMF and DMAC.

In another embodiment, the film-forming coating polymer is a thermoplastic polymer that is melted, enters the pores of the elastomeric matrix and, upon cooling or solidifying, forms a coating on at least a portion of the solid material of the elastomeric matrix. In another embodiment, the processing temperature of the thermoplastic coating polymer in its melted form is above about 60° C. In another embodiment, the processing temperature of the thermoplastic coating polymer in its melted form is above about 90° C. In another embodiment, the processing temperature of the thermoplastic coating polymer in its melted form is above about 120° C.

In a further embodiment of the invention, described in more detail below, some or all of the pores of the elastomeric matrix are coated or filled with a cellular ingrowth promoter. In another embodiment, the promoter can be foamed. In another embodiment, the promoter can be present as a film. The promoter can be a biodegradable material to promote cellular invasion of the elastomeric matrix in vivo. Promoters include naturally occurring materials that can be enzymatically degraded in the human body or are hydrolytically unstable in the human body, such as fibrin, fibrinogen, collagen, elastin, hyaluronic acid and absorbable biocompatible polysaccharides, such as chitosan, starch, fatty acids (and esters thereof), glucoso-glycans and hyaluronic acid. In some embodiments, the pore surface of the elastomeric matrix is coated or impregnated, as described above, but substituting the promoter for the biocompatible polymer or adding the promoter to the biocompatible polymer, to encourage cellular ingrowth and proliferation.

In one embodiment, the coating or impregnating process is conducted so as to ensure that the product "composite elastomeric implantable device", i.e., a reticulated elastomeric matrix and a coating, as used herein, retains sufficient resiliency after compression such that it can be delivery-device delivered, e.g., catheter, syringe or endoscope delivered. Some embodiments of such a composite elastomeric implantable device will now be described with reference to collagen, by way of non-limiting example, with the understanding that other materials may be employed in place of collagen, as described above.

Collagen may be infiltrated by forcing, e.g., with pressure, an aqueous collagen slurry, suspension or solution into the pores of an elastomeric matrix. The collagen may be Type I, II or III or mixtures thereof. In one embodiment, the collagen type comprises at least 90% collagen I. The concentration of collagen is from about 0.3% to about 2.0% by weight and the pH of the slurry, suspension or solution is adjusted to be from about 2.6 to about 5.0 at the time of lyophilization. Alternatively, collagen may be infiltrated by dipping an elastomeric matrix into a collagen slurry.

As compared with the uncoated reticulated elastomer, the composite elastomeric implantable device can have a void phase that is slightly reduced in volume. In one embodiment, the composite elastomeric implantable device retains good fluid permeability and sufficient porosity for ingrowth and proliferation of fibroblasts or other cells.

Optionally, the lyophilized collagen can be crosslinked to control the rate of in vivo enzymatic degradation of the collagen coating and to control the ability of the collagen coating to bond to the elastomeric matrix. Without being bound by any particular theory, it is thought that when the composite elastomeric implantable device is implanted, tissue-forming agents that have a high affinity to collagen, such as fibroblasts, will more readily invade the collagen-impregnated elastomeric matrix than the uncoated matrix. It is further thought, again without being bound by any particular theory, that as the collagen enzymatically degrades, new tissue invades and fills voids left by the degrading collagen while also infiltrating and filling other available spaces in the elastomeric matrix. Such a collagen coated or impregnated elastomeric matrix is thought, without being bound by any particular theory, to be additionally advantageous for the structural integrity provided by the reinforcing effect of the collagen within the pores of the elastomeric matrix which can impart greater rigidity and structural stability to various configurations of the elastomeric matrix.

The biodurable reticulated elastomeric matrix useful according to this invention can support cell types including cells secreting structural proteins and cells that produce proteins characterizing organ function. The ability of the elastomeric matrix to facilitate the co-existence of multiple cell types together and its ability to support protein secreting cells demonstrates the applicability of the elastomeric matrix in organ growth in vitro or in vivo and in organ reconstruction. In addition, the biodurable reticulated elastomeric matrix may also be used in the scale up of human cell lines for implantation to the body for many applications including implantation of fibroblasts, chondrocytes, osteoblasts, osteoclasts, osteocytes, synovial cells, bone marrow stromal cells, stem cells, fibrocartilage cells, endothelial cells, smooth muscle cells, adipocytes, cardiomyocytes, myocytes, keratinocytes, hepatocytes, leukocytes, macrophages, endocrine cells, genitourinary cells, lymphatic vessel cells, pancreatic islet cells, muscle cells, intestinal cells, kidney cells, blood vessel cells, thyroid cells, parathyroid cells, cells of the adrenal-hypothalamic pituitary axis, bile duct cells, ovarian or testicular cells, salivary secretory cells, renal cells, epithelial cells, nerve cells, stem cells, progenitor cells, myoblasts and intestinal cells.

New tissue can be obtained through implantation of cells seeded in elastomeric matrices (either prior to or concurrent to or subsequent to implantation). In this case, the elastomeric matrices may be configured either in a closed manner to protect the implanted cells from the body's immune system, or in an open manner so that the new cells can be incorporated into the body. Thus in another embodiment, the cells may be incorporated, i.e., cultured and proliferated, onto the elastomeric matrix prior, concurrent or subsequent to implantation of the elastomeric matrix in the patient.

In one embodiment, the implantable device made from biodurable reticulated elastomeric matrix can be seeded with a type of cell and cultured before being inserted into the patient, optionally using a delivery-device, for the explicit purpose of tissue repair or tissue regeneration. It is necessary to perform the tissue or cell culture in a suitable culture medium with or without stimulus such as stress or orientation. The cells include fibroblasts, chondrocytes, osteoblasts, osteoclasts, osteocytes, synovial cells, bone marrow stromal cells, stem cells, fibrocartilage cells, endothelial cells and smooth muscle cells.

Surfaces on the biodurable reticulated elastomeric matrix possessing different pore morphology, size, shape and orientation may be cultured with different type of cells to develop cellular tissue engineering implantable devices that are specifically targeted towards orthopedic applications, especially in soft tissue attachment, repair, regeneration, augmentation and/or support encompassing spine, shoulder, knee, hand, joints, and in the growth of a prosthetic organ. In another embodiment, all the surfaces on the biodurable reticulated elastomeric matrix possessing similar pore morphology, size, shape and orientation may be so cultured.

In another embodiment, the film-forming polymer used to coat the reticulated elastomeric matrix can provide a vehicle for the delivery of and/or the controlled release of a pharmaceutically-active agent, for example, a drug, such as is described in the copending applications. In another embodiment, the pharmaceutically-active agent is admixed with, covalently bonded to and/or adsorbed in or on the coating of the elastomeric matrix to provide a pharmaceutical composition. In another embodiment, the components, polymers and/or blends used to form the foam comprise a pharmaceutically-active agent. To form these foams, the previously described components, polymers and/or blends are admixed with the pharmaceutically-active agent prior to forming the foam or the pharmaceutically-active agent is loaded into the foam after it is formed.

In one embodiment, the coating polymer and pharmaceutically-active agent have a common solvent. This can provide a coating that is a solution. In another embodiment, the pharmaceutically-active agent can be present as a solid dispersion in a solution of the coating polymer in a solvent.

A reticulated elastomeric matrix comprising a pharmaceutically-active agent may be formulated by mixing one or more pharmaceutically-active agent with the polymer used to make the foam, with the solvent or with the polymer-solvent mixture and foamed. Alternatively, a pharmaceutically-active agent can be coated onto the foam, in one embodiment, using a pharmaceutically-acceptable carrier. If melt-coating is employed, then, in another embodiment, the pharmaceutically-active agent withstands melt processing temperatures without substantial diminution of its efficacy.

Formulations comprising a pharmaceutically-active agent can be prepared by admixing, covalently bonding and/or adsorbing one or more pharmaceutically-active agents with the coating of the reticulated elastomeric matrix or by incorporating the pharmaceutically-active agent into additional hydrophobic or hydrophilic coatings. The pharmaceutically-active agent may be present as a liquid, a finely divided solid or another appropriate physical form. Typically, but optionally, the matrix can include one or more conventional additives, such as diluents, carriers, excipients, stabilizers and the like.

In another embodiment, a top coating can be applied to delay release of the pharmaceutically-active agent. In another embodiment, a top coating can be used as the matrix for the delivery of a second pharmaceutically-active agent. A layered coating, comprising respective layers of fast- and slow-hydrolyzing polymer, can be used to stage release of the pharmaceutically-active agent or to control release of different pharmaceutically-active agents placed in the different layers. Polymer blends may also be used to control the release rate of different pharmaceutically-active agents or to provide a desirable balance of coating characteristics (e.g., elasticity, toughness) and drug delivery characteristics (e.g., release profile). Polymers with differing solvent solubilities can be used to build-up different polymer layers that may be used to deliver different pharmaceutically-active agents or to control the release profile of a pharmaceutically-active agents.

The amount of pharmaceutically-active agent present depends upon the particular pharmaceutically-active agent employed and medical condition being treated. In one embodiment, the pharmaceutically-active agent is present in an effective amount. In another embodiment, the amount of pharmaceutically-active agent represents from about 0.01% to about 60% of the coating by weight. In another embodiment, the amount of pharmaceutically-active agent represents from about 0.01% to about 40% of the coating by weight. In another embodiment, the amount of pharmaceutically-active agent represents from about 0.1% to about 20% of the coating by weight.

Many different pharmaceutically-active agents can be used in conjunction with the reticulated elastomeric matrix. In general, pharmaceutically-active agents that may be administered via pharmaceutical compositions of this invention include, without limitation, any therapeutic or pharmaceutically-active agent (including but not limited to nucleic acids, proteins, lipids, and carbohydrates) that possesses desirable physiologic characteristics for application to the implant site or administration via a pharmaceutical compositions of the invention. Therapeutics include, without limitation, antiinfectives such as antibiotics and antiviral agents; chemotherapeutic agents (e.g., anticancer agents); anti-rejection agents; analgesics and analgesic combinations; anti-inflammatory agents; hormones such as steroids; growth factors (including but not limited to cytokines, chemokines, and interleukins) and other naturally derived or genetically engineered proteins, polysaccharides, glycoproteins and lipoproteins. These growth factors are described in The Cellular and Molecular Basis of Bone Formation and Repair by Vicki Rosen and R. Scott Thies, published by R. G. Landes Company, hereby incorporated herein by reference. Additional therapeutics include thrombin inhibitors, antithrombogenic agents, thrombolytic agents, fibrinolytic agents, vasospasm inhibitors, calcium channel blockers, vasodilators, antihypertensive agents, antimicrobial agents, antibiotics, inhibitors of surface glycoprotein receptors, antiplatelet agents, antimitotics, microtubule inhibitors, anti secretory agents, actin inhibitors, remodeling inhibitors, antisense nucleotides, anti metabolites, antiproliferatives, anticancer chemotherapeutic agents, anti-inflammatory steroids, non-steroidal anti-inflammatory agents, immunosuppressive agents, growth hormone antagonists, growth factors, dopamine agonists, radiotherapeutic agents, peptides, proteins, enzymes, extracellular matrix components, angiotensin-converting enzyme (ACE) inhibitors, free radical scavengers, chelators, antioxidants, anti polymerases, antiviral agents, photodynamic therapy agents and gene therapy agents.

Additionally, various proteins (including short chain peptides), growth agents, chemotatic agents, growth factor receptors or ceramic particles can be added to the foams during processing, adsorbed onto the surface or back-filled into the foams after the foams are made. For example, in one embodiment, the pores of the foam may be partially or completely filled with biocompatible resorbable synthetic polymers or biopolymers (such as collagen or elastin), biocompatible ceramic materials (such as hydroxyapatite), and combinations thereof, and may optionally contain materials that promote tissue growth through the device. Such tissue-growth materials include but are not limited to autograft, allograft or xenograft bone, bone marrow and morphogenic proteins. Biopolymers can also be used as conductive or chemotactic materials, or as delivery vehicles for growth factors. Examples include recombinant collagen, animal-derived collagen, elastin and hyaluronic acid. Pharmaceutically-active coatings or surface treatments could also be present on the surface of the materials. For example, bioactive peptide sequences (RGD's) could be attached to the surface to facilitate protein adsorption and subsequent cell tissue attachment.

Bioactive molecules include, without limitation, proteins, collagens (including types IV and XVIII), fibrillar collagens (including types I, II, III, V, XI), FACIT collagens (types IX, XII, XIV), other collagens (types VI, VII, XIII), short chain collagens (types VIII, X), elastin, entactin-1, fibrillin, fibronectin, fibrin, fibrinogen, fibroglycan, fibromodulin, fibulin, glypican, vitronectin, laminin, nidogen, matrilin, perlecan, heparin, heparan sulfate proteoglycans, decorin, filaggrin, keratin, syndecan, agrin, integrins, aggrecan, biglycan, bone sialoprotein, cartilage matrix protein, Cat-301 proteoglycan, CD44, cholinesterase, HB-GAM, hyaluronan, hyaluronan binding proteins, mucins, osteopontin, plasminogen, plasminogen activator inhibitors, restrictin, serglycin, tenascin, thrombospondin, tissue-type plasminogen activator, urokinase type plasminogen activator, versican, von Willebrand factor, dextran, arabinogalactan, chitosan, polyactideglycolide, alginates, pullulan, gelatin and albumin.

Additional bioactive molecules include, without limitation, cell adhesion molecules and matricellular proteins, including those of the immunoglobulin (Ig; including monoclonal and polyclonal antibodies), cadherin, integrin, selectin, and H-CAM superfamilies. Examples include, without limitation, AMOG, CD2, CD4, CD8, C-CAM (CELL-CAM 105), cell surface galactosyltransferase, connexins, desmocollins, desmoglein, fasciclins, F11, GP Ib-IX complex, intercellular adhesion molecules, leukocyte common antigen protein tyrosine phosphate (LCA, CD45), LFA-1, LFA-3, mannose binding proteins (MBP), MTJC18, myelin associated glycoprotein (MAG), neural cell adhesion molecule (NCAM), neurofascin, neruoglian, neurotactin, netrin, PECAM-1, PH-20, semaphorin, TAG-1, VCAM-1, SPARC/osteonectin, CCN1 (CYR61), CCN2 (CTGF; Connective Tissue Growth Factor), CCN3 (NOV), CCN4 (WISP-1), CCN5 (WISP-2), CCN6 (WISP-3), occludin and claudin. Growth factors include, without limitation, BMP's (1-7), BMP-like Proteins (GFD-5, -7, -8), epidermal growth factor (EGF), erythropoietin (EPO), fibroblast growth factor (FGF), growth hormone (GH), growth hormone releasing factor (GHRF), granulocyte colony-stimulating factor (G-CSF), granulocyte-macrophage colony-stimulating factor (GM-CSF), insulin, insulin-like growth factors (IGF-I, IGF-II), insulin-like growth factor binding proteins (IGFBP), macrophage colony-stimulating factor (M-CSF), Multi-CSF (II-3), platelet-derived growth factor (PDGF), tumor growth factors (TGF-alpha, TGF-beta), tumor necrosis factor (TNF-alpha), vascular endothelial growth factors (VEGF's), angiopoietins, placenta growth factor (PIGF), interleukins, and receptor proteins or other molecules that are known to bind with the aforementioned factors. Short-chain peptides include, without limitation (designated by single letter amino acid code), RGD, EILDV, RGDS, RGES, RFDS, GRDGS, GRGS, GRGDTP and QPPRARI.

The elastomeric matrix useful according to the invention may be molded into any of a wide variety of shapes and sizes during its formation or production. The shape may be a working configuration, such as any of the shapes and configurations described above, or the shape may be for bulk stock. Stock items may subsequently be cut, trimmed, punched or otherwise shaped for end use. The sizing and shaping can be carried out by, for example, using a blade, punch, drill or laser. In each of these embodiments, the processing temperature or temperatures of the cutting tools for shaping and sizing can be greater than about 100° C. In another embodiment, the processing temperature(s) of the cutting tools for shaping and sizing can be greater than about 130° C. Finishing steps can include, in one embodiment, trimming of macrostructural surface protrusions, such as struts or the like, which can irritate biological tissues. In another embodiment, finishing steps can include heat annealing. Annealing can be carried out before or after final cutting and shaping.

The dimensions of the shaped and sized devices made from the elastomeric matrix can vary depending on the application. In one embodiment, major dimensions of a device prior to being compressed and delivered are from about 20 mm to about 30 mm in one direction and from about 20 mm to about 30 mm in another direction. The length of a cylindrical portion of a device according to the invention is expected to be from about 6 mm to about 10 mm, since that is approximately the typical radial thickness of a patient's annulus. The elastomeric matrix can exhibit compression set upon being compressed and transported through a delivery-device, e.g., a trocar, cannula, or catheter, with assisted visualization. In another embodiment, compression set and its standard deviation are taken into consideration when designing the pre-compression dimensions of the device.

Biodurable reticulated elastomeric matrices, or an implantable device system comprising such matrices, can be sterilized by any method known to the art including gamma irradiation, autoclaving, ethylene oxide sterilization, infrared irradiation and electron beam irradiation. In one embodiment, biodurable elastomers used to fabricate the elastomeric matrix tolerate such sterilization without loss of useful physical and mechanical properties. The use of gamma irradiation can potentially provide additional crosslinking to enhance the performance of the device.

In one embodiment, the sterilized products may be packaged in sterile packages of paper, polymer or other suitable material. In another embodiment, within such packages, the elastomeric matrix is compressed within a retaining member to facilitate its loading into a delivery-device, such as a catheter or endoscope, in a compressed configuration. In another embodiment, the elastomeric matrix comprises an elastomer with a compression set enabling it to expand to a substantial proportion of its pre-compressed volume, e.g., at 25° C., to at least 50% of its pre-compressed volume. In another embodiment, expansion occurs after the elastomeric matrix remains compressed in such a package for typical commercial storage and distribution times, which will commonly exceed 3 months and may be up to 1 or 5 years from manufacture to use.

In one embodiment, an implantable device according to the invention may be rendered radio-opaque to facilitate in vivo imaging, for example, by adhering to, covalently bonding to and/or incorporating into the elastomeric matrix itself particles of a radio-opaque material. Radio-opaque materials include titanium, tantalum, tungsten, barium sulfate or other suitable material known to those skilled in the art.

According to the invention the reticulated elastomeric matrix can be appropriately shaped to form a closure device to seal the access opening in the annulus resulting from a discotomy to reinforce and stabilize the disc annulus in case of herniated disc, also known as disc prolapse or a slipped or bulging disc. The implantable device is compressed and delivered into the annulus opening by a trocar, cannula, or catheter with assisted visualization through an endoscopic intrument such as a laproscope, arthroscope, or cystoscope, preferably the cannula used during the discectomy procedure. The device can be secured into the opening by at least the following two mechanisms: first, the outwardly resilient nature of the reticulated solid phase can provide a mechanical means for preventing migration; and, second, the reticulated solid phase can serve as a scaffold to support fibrocartilage growth into the interconnected void phase of the elastomeric matrix. Additional securing may be obtained by the use of anchors, sutures or biological glues and adhesives, as known to those in the art. The closure device can support fibrocartilage ingrowth into the elastomeric matrix of the implantable device. Once released at the site, the reticulated elastomeric matrix expands resiliently to about its original, relaxed size and shape subject, of course, to its compression set limitation and any desired flexing, draping or other conformation to the site anatomy that the implantable device may adopt.

In one embodiment, cellular entities such as fibroblasts and tissues can invade and grow into the reticulated elastomeric matrix. In due course, such ingrowth can extend into the interior pores and interstices of the inserted reticulated elastomeric matrix. Eventually, the elastomeric matrix can become substantially filled with proliferating cellular ingrowth that provides a mass that can occupy the site or the void spaces in it. The types of tissue ingrowth possible include, but are not limited to, fibrous tissues and endothelial tissues.

In another embodiment, the implantable device or device system causes cellular ingrowth and proliferation throughout the site, throughout the site boundary, or through some of the exposed surfaces, thereby sealing the site. Over time, this induced fibrovascular entity resulting from tissue ingrowth can cause the implantable device to be incorporated into the conduit. Tissue ingrowth can lead to very effective resistance to migration of the implantable device over time. It may also prevent recanalization of the conduit. In another embodiment, over the course of time, for example, for 2 weeks to 3 months to 1 year, the implanted reticulated elastomeric matrix becomes completely filled and/or encapsulated by tissue, fibrous tissue, scar tissue or the like.

The properties of the reticulated elastomeric matrix can be engineered to match the application by, e.g., controlling the amount of crosslinking, amount of crystallinity, chemical composition, chemical type of the solvent or solvent blend (when a solvent is used in processing), annealing conditions, curing conditions, and degree of reticulation. Unlike biodegradable polymers, when used as a scaffold, the reticulated elastomeric matrix maintains its physical characteristics and performance in vivo over long periods of time. Thus, it does not initiate undesirable tissue response as is observed for biodegradable implants when they break down and degrade. The high void content and degree of reticulation of the reticulated elastomeric matrix allows tissue ingrowth and proliferation of cells within the matrix. In one embodiment, the ingrown tissue and/or proliferated cells occupy from about 51% to about 99% of the volume of interconnected void phase of the original implantable device, thereby providing functionality, such as load bearing capability, of the original tissue that is being repaired or replaced.

EXAMPLES

Example 1

Fabrication of a Crosslinked Reticulated Polyurethane Matrix

Aromatic isocyanates, RUBINATE 9258 (from Huntsman; comprising a mixture of 4,4'-MDI and 2,4'-MDI), were used as the isocyanate component. RUBINATE 9258 contains about 68% by weight 4,4'-MDI, about 32% by weight 2,4'-MDI and has an isocyanate functionality of about 2.33 and is a liquid at 25° C. A polyol—1,6-hexamethylene carbonate (PC 1733, Stahl Chemicals) i.e., a diol, with a molecular weight of about 1,000 Daltons, was used as the polyol component and is a solid at 25° C. Glycerol was the chain extender, and water was used as the blowing agent. The blowing catalyst were tertiary amine 33% triethylenediamine in dipropylene glycol (DABCO 33LV supplied by Air Products) and Niax-A1 (supplied by Air Products). A silicone-based surfactant was used (TEGOSTAB® BF 2370, supplied by Goldschmidt). The cell-opener was ORTEGOL® 501 (supplied by Goldschmidt). A viscosity depressant (Propylene carbonate supplied by Sigma-Aldrich) was also used. The proportions of the components that were used is given in the following table:

TABLE 1

| Ingredient | Parts by Weight |
| --- | --- |
| Polyol Component - PC 1733, Stahl Chemicals Glycerine | 100 |
| | 4.92 |
| Viscosity Depressant - Propylene carbonate | 11.6 |
| Surfactant - TEGOSTAB ® BF 2370 | 4.40 |
| Cell Opener - ORTEGOL ® 501 | 4.0 |
| Isocyanate Component RUBINATE 9258 | 99.78 |
| Isocyanate Index | 1.00 |
| Distilled Water | 3.36 |
| Blowing Catalyst Dabco 33 LV | 1.0 |
| Blowing Catalyst Niax-A1 | 0.06 |

The polyol was liquefied at 70° C. in an air circulation oven, and was weighed into a polyethylene cup. Viscosity depressant (propylene carbonate) was added to the polyol and mixed with a drill mixer equipped with a mixing shaft at 3100 rpm for 15 seconds (mix-1). Surfactant (Tegostab BF-2370) was added to mix-1 and mixed for additional 15 seconds (mix-2). Cell opener (Ortogel 501) was added to mix-2 and mixed for 15 seconds (mix-3). Isocyanate (Rubinate 9258) was added to mix-3 and mixed for 60±10 seconds (system A).

Distilled water was mixed with both blowing catalyst (Dabco 33LV and Niax A1) and glycerine in a small plastic cup by using a tiny glass rod for 60 seconds (System B).

System B was poured into System A as quickly as possible without spilling and with vigorous mixing with a drill mixer for 10 seconds and poured into cardboard box of 9 in.×8 in.×5 in., which is covered inside with aluminum foil. The foaming profile was as follows: mixing time of 10 sec., cream time of 18 sec. and rise time of 75 sec.

Two minutes after beginning of foam mixing, the foam was placed in the oven at 100-105° C. for curing for 65 minutes. The foam was taken from the oven and cooled for 15 minutes at room temperature. The skin was cut with the band saw, and the foam was pressed by hand from all sides to open the cell windows. The foam was put back into an air-circulation oven for post-curing at 100° C.-105° C. for an additional 5 hours.

Figure 8:
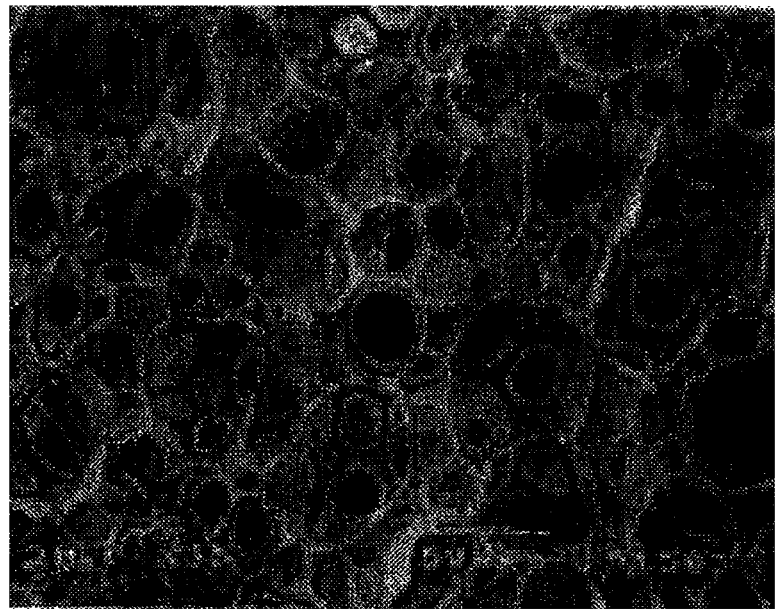
FIGS. 8 and 9 are each a micrograph of material prepared according to Example 1.
Figure 9:

The average pore diameter of the foam, as observed by optical microscopy, as shown in the micrographs of FIGS. 8 and 9, was between 150 and 300 μm.

The subsequent foam testing was carried out in accordance with ASTM D3574. Density was measured with specimens measuring 50 mm×50 mm×25 mm. The density was calculated by dividing the weight of the sample by the volume of the specimen; a value of 2.75 lbs/ft$^3$ was obtained.

Tensile tests were conducted on samples that were cut both parallel and perpendicular to the direction of foam rise. The dog-bone shaped tensile specimens were cut from blocks of foam each about 12.5 mm thick, about 25.4 mm wide and about 140 mm long. Tensile properties (strength and elongation at break) were measured using an INSTRON Universal Testing Instrument Model 1122 with a cross-head speed of 500 mm/min (19.6 inches/minute). The average tensile strength, measured from two orthogonal directions parallel and perpendicular with respect to foam rise, were 67.6 psi and 56.44 psi, respectively. The elongation to break was approximately 46%.

In the subsequent reticulation procedure, a block of foam was placed into a pressure chamber, the doors of the chamber were closed and an airtight seal was maintained. The pressure was reduced to remove substantially all of the air in the foam. A combustible ratio of hydrogen to oxygen gas was charged into the chamber for enough time to permeate all the samples. The gas in the chamber was then ignited by a spark plug. The ignition exploded the gasses within the foam cell structure. This explosion blew out many of the foam cell windows, thereby creating a reticulated elastomeric matrix structure.

Example 2

Fabrication of a Crosslinked Reticulated Polyurethane Matrix

Aromatic isocyanates, RUBINATE 9258 (from Huntsman; comprising a mixture of 4,4'-MDI and 2,4'-MDI), were used as the isocyanate component. RUBINATE 9258 contains about 68% by weight 4,4'-MDI, about 32% by weight 2,4'-MDI and has an isocyanate functionality of about 2.33 and is a liquid at 25° C. A polyol—1,6-hexamethylene carbonate (Desmophen LS 2391, Bayer Polymers), i.e., a diol, with a molecular weight of about 2,000 Daltons, was used as the polyol component and is a solid at 25° C. Water was used as the blowing agent. The blowing catalyst was the tertiary amine 33% triethylenediamine in dipropylene glycol (DABCO 33LV supplied by Air Products). A silicone-based surfactant was used (TEGOSTAB® BF 2370, supplied by Goldschmidt). The cell-opener was ORTEGOL® 501 (supplied by Goldschmidt). A viscosity depressant (Propylene carbonate supplied by Sigma-Aldrich) was also used. The proportions of the components that were used is given the following table:

TABLE 2

| Ingredient | Parts by Weight |
| --- | --- |
| Polyol Component - Desmophen LS 2391 | 100 |
| Viscosity Depressant - Propylene carbonate | 5.76 |
| Surfactant - TEGOSTAB ® BF 2370 | 2.16 |
| Cell Opener - ORTEGOL ® 501 | 0.48 |
| Isocyanate Component RUBINATE 2391 | 53.8 |
| Isocyanate Index | 1.00 |
| Distilled Water | 2.82 |
| Blowing Catalyst | 0.44 |

The polyol Desmophen LS 2391 was liquefied at 70° C. in an air circulation oven, and 150 gms of it was weighed into a polyethylene cup. 8.7 g of viscosity depressant (propylene carbonate) was added to the polyol and mixed with a drill mixer equipped with a mixing shaft at 3100 rpm for 15 seconds (mix-1). 3.3 g of surfactant (Tegostab BF-2370) was added to mix-1 and mixed for additional 15 seconds (mix-2). 0.75 g of cell opener (Ortogel 501) was added to mix-2 and mixed for 15 seconds (mix-3). 80.9 g of isocyanate (Rubinate 9258) is added to mix-3 and mixed for 60±10 seconds (System A).

4.2 g of distilled water was mixed with 0.66 g of blowing catalyst (Dabco 33LV) in a small plastic cup by using a tiny glass rod for 60 seconds (System B).

System B was poured into System A as quickly as possible without spilling and with vigorous mixing with a drill mixer for 10 seconds and poured into cardboard box of 9 in.×8 in.×5 in., which was covered inside with aluminum foil. The foaming profile was as follows: mixing time of 10 sec., cream time of 18 sec. and rise time of 85 sec.

Two minutes after beginning of foam mixing, the foam was placed in the oven at 100-105° C. for curing for 60 minutes. The foam was taken from the oven and cooled for 15 minutes at room temperature. The skin was cut with the band saw, and the foam was pressed by hand from all sides to open the cell windows. The foam was put back in an air-circulation oven for post-curing at 100-105° C. for an additional 5 hours.

Figure 10:
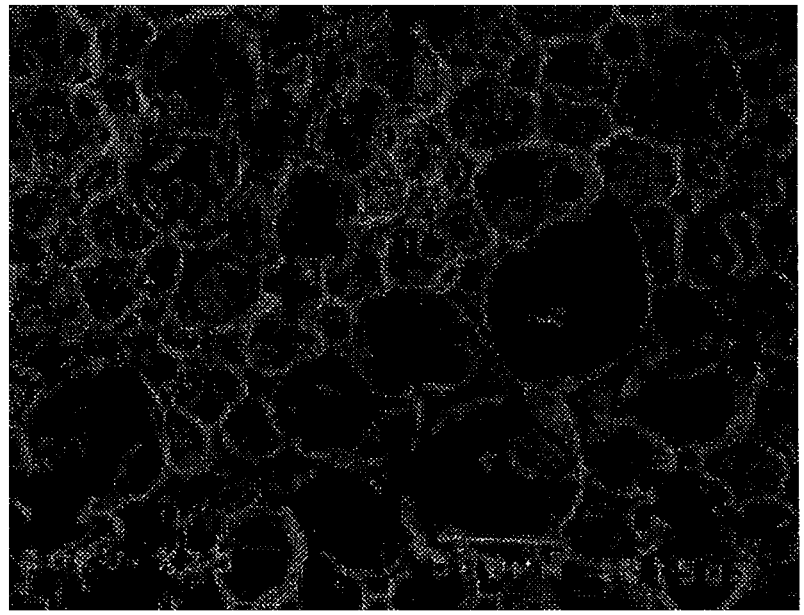
FIGS. 10 and 11 are each a micrograph of material prepared according to Example 2.
Figure 11:
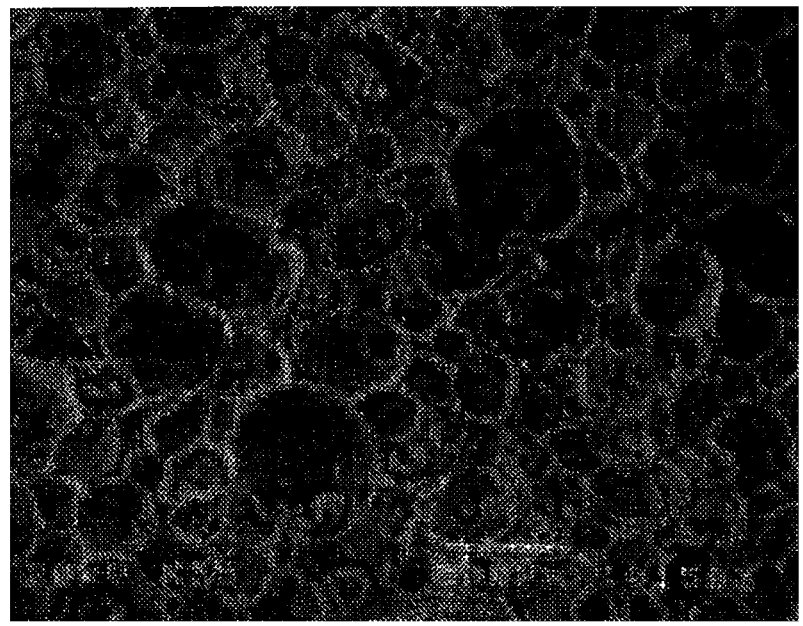

The average pore diameter of the foam, as observed by optical microscopy, as shown in FIGS. 10 and 11, was between 150 and 450 μm.

Subsequent foam testing was carried out in accordance with ASTM D3574. Density was measured with specimens measuring 50 mm×50 mm×25 mm. The density was calculated by dividing the weight of the sample by the volume of the specimen; a value of 2.5 lbs/ft$^3$ was obtained.

Tensile tests were conducted on samples that were cut both parallel and perpendicular to the direction of foam rise. The dog-bone shaped tensile specimens were cut from blocks of foam each about 12.5 mm thick, about 25.4 mm wide and about 140 mm long. Tensile properties (strength and elongation at break) were measured using an INSTRON Universal Testing Instrument Model 1122 with a cross-head speed of 500 mm/min (19.6 inches/minute). The average tensile strength, measured from two orthogonal directions with respect to foam rise, was 24.64±2.35 psi. The elongation to break was approximately 215±12%.

Compressive strengths of the foam were measured with specimens measuring 50 mm×50 mm×25 mm. The tests were conducted using an INSTRON Universal Testing Instrument Model 1122 with a cross-head speed of 10 mm/min (0.4 inches/min). The compressive strength at 50% was about 12±3 psi. The compression set after subjecting the sample to 50% compression for 22 hours at 40° C. and releasing the stress was 2%.

Tear resistance strength of the foam was measured with specimens measuring approximately 152 mm×25 mm×12.7 mm. A 40 mm cut was made on one side of each specimen. The tear strength was measured using an INSTRON Universal Testing Instrument Model 1122 with a cross-head speed of 500 mm/min (19.6 inches/minute). The tear strength was determined to be about 2.9±0.1 lbs/inch.

The pore structure and its inter-connectivity is measured by Liquid Extrusion Porosimeter (manufactured by Porous Materials, Inc. (Ithaca, N.Y.). In this test, the pores of a 25.4 mm diameter sample is filled with a wetting fluid having a surface tension of 19 dynes/cm and loaded in a sample chamber with a 27 micron diameter pore membrane being placed under the sample. The pressure of air in the chamber space above the wetted sample is increased slowly so that the liquid is extruded from the pores of the sample. For low surface tension fluid, the contact angle is taken to be zero and the wetting liquid that spontaneously fills the pore of the test sample also spontaneously fill the pores of the membranes when the former is emptied under pressure with larger pores emptying out at lower pressures and smaller pores emptying out at higher pressure. The displaced liquid passes through the membrane and its volume measured. The differential pressure p required to displace liquid from a pore is related to its diameter D, surface tension of the liquid $\gamma$ and the contact angle $\theta$ by the relation $p=4\gamma \cos \theta/D$. The gas pressure gives the pore diameter and the volume of the displaced liquid gives the pore volume or the intrusion volume accessible to the low surface tension liquid. Again measurement of liquid flow (water in this case) without the membrane under the sample and using similar pressure-flow methods yields liquid permeability. The liquid intrusion volume for the foam is 4 cc/gm and permeability of water through the foam is 1 lit/min/psi/sq cm.

In the subsequent reticulation procedure, a block of foam was placed into a pressure chamber, the doors of the chamber are closed, and an airtight seal was maintained. The pressure is reduced to remove substantially all of the air in the foam. A combustible ratio of hydrogen to oxygen gas was charged into the chamber for enough time to permeate all the samples. The gas in the chamber was then ignited by a spark plug. The ignition explodes the gasses within the foam cell structure. This explosion blew out many of the foam cell windows, thereby creating a reticulated elastomeric matrix structure.

Tensile tests were conducted on reticulated samples that were cut both parallel and perpendicular to the direction of foam rise. The dog-bone shaped tensile specimens were cut from blocks of foam each about 12.5 mm thick, about 25.4 mm wide and about 140 mm long. Tensile properties (strength and elongation at break) were measured using an INSTRON Universal Testing Instrument Model 1122 with a cross-head speed of 500 mm/min (19.6 inches/minute). The average tensile strength, measured from two orthogonal directions with respect to foam rise, was 23.5 psi. The elongation to break was approximately 194%.

Post reticulation compressive strengths of the foam were measured with specimens measuring 50 mm×50 mm×25 mm. The tests were conducted using an INSTRON Universal Testing Instrument Model 1122 with a cross-head speed of 10 mm/min (0.4 inches/min). The compressive strength at 50% was about 6.5 psi.

The pore structure and its inter-connectivity is measured by Liquid Extrusion Porosimeter. The liquid intrusion volume for the reticulated foam is 28 cc/gm and permeability of water through the foam is 413 lit/min/psi/sq cm. The results demonstrate the interconnected and continuous pore structure of the reticulated foam compared to the un-reticulated foam.

While illustrative embodiments of the invention have been described above, it is, of course, understood that many and various modifications will be apparent to those in the relevant art, or may become apparent as the art develops. Such modifications are contemplated as being within the spirit and scope of the invention or inventions disclosed in this specification.

We claim:

1. A method of treating spinal annular defects which comprise the steps of: (a) inserting an at least partially cylindrical apparatus comprising a scaffold comprised of a biodurable, resiliently compressible, elastomeric reticulated matrix into the lumen of a delivery means; (b) advancing the distal tip of the delivery means into an opening in an annulus; (c) advancing the apparatus through the lumen into the opening; and (d) withdrawing the delivery means, whereby the apparatus expands into the opening.

2. The apparatus of method of claim 1, wherein the elastomeric matrix is hydrophobic.

3. The method of claim 1, wherein the elastomeric matrix comprises an elastomer selected from the group consisting of polycarbonate polyurethanes, polyester polyurethanes, polyether polyurethanes, polysiloxane polyurethanes, polyurethanes with mixed soft segments, polycarbonates, polyesters, polyethers, polysiloxanes, polyurethanes, and mixtures of two or more thereof.

4. The method of claim 3, wherein the elastomeric matrix comprises a polycarbonate polyurethane.

5. method of claim 3, wherein the elastomer is prepared by reacting a polyol component with an isocynanate component.

6. The method of claim 5, wherein the polyol component comprises a polycarbonate polyol, hydrocarbon polyol, polysiloxane polyol, poly(carbonate-co-hydrocarbon) polyol, poly(carbonate-co-siloxane) polyol, poly(hydrocarbon-co-siloxane) polyol, or mixtures thereof.

7. The method of claim 5, wherein the polyol component comprises a difunctional polycarbonate diol.

8. The method of claim 5, wherein the isocyanate component comprises tetramethylene diisocyanate, cyclohexane-1,2-diisocyanate, cyclohexane-1,4-diisocyanate, hexamethylene diisocyanate, isophorone diisocyanate, methylene-bis-(p-cyclohexyl isocyanate), p-phenylene diisocyanate, 4,4'-diphenylmethane diisocyanate, 2,4'-diphenylmethane diisocyanate, 2,4-toluene diisocyanate, 2,6-toluene diisocyanate, m-tetramethylxylene diisocyanate, or mixtures thereof.

9. The method of claim 5, wherein the isocyanate component comprises MDI, wherein the MDI is a mixture of at least about 5% by weight of 2,4'-MDI with the balance 4,4'-MDI.

10. The method of claim 1, wherein the elastomeric matrix comprises a polyurethane.

11. The method of claim 1, wherein the elastomeric matrix comprises a reticulated elastomeric matrix comprising a plurality of pores, the pores having an average diameter or other largest transverse dimension of at least about 20 µm.

12. The method of claim 11, wherein the pores have an average diameter or other largest transverse dimension of from about 20 µm to about 150 µm.

13. The method of claim 11, wherein the pores have an average diameter or other largest transverse dimension of from about 150 μm to about 250 μm.

14. The method of claim 11, wherein the pores have an average diameter or other largest transverse dimension of from about 250 μm to about 500 μm.

15. The method of claim 1, wherein, when the elastomeric matrix is compressed from a relaxed configuration to a first, compact configuration for delivery via a delivery-device, it expands to a second, working configuration, in vivo, at least about 80% claim of the size of the relaxed configuration in at least one dimension.

16. The method of claim 15, wherein the recovery properties of the elastomeric matrix are such that a dimension of the second, working configuration is within about 20% of a relaxed dimension of the relaxed configuration after compression to from about 50 to about 10% of the relaxed dimension.

17. The method of claim 1, wherein the elastomeric matrix has a compressive strength at 50% compression of from about 1 to about 500 psi, a tensile strength of from about 1 to about 500 psi, and an ultimate tensile elongation of at least about 46%.

18. The method of claim 1, wherein the elastomeric matrix has a compression set after 22 hours compression at about 25° C. to 25% of its thickness in one dimension of not more than about 20%.

19. The method of claim 1, wherein the reticulated elastomeric matrix is configured to permit cellular ingrowth and proliferation into the elastomeric matrix.

20. The method of claim 1, endoporously coating a reticulated elastomeric matrix with a coating material selected to encourage cellular ingrowth and proliferation.

21. The method of claim 1, wherein the coating material comprises a foamed coating of a biodegradable material, the biodegradable material comprising collagen, fibronectin, elastin, hyaluronic acid or mixtures thereof.

22. The method of claim 1, wherein the implantable device comprises a plurality of elastomeric matrices.

23. The method of claim 1, wherein the delivery means is a trocar, cannula, or catheter, with visual assistance through an endoscopic instrument.

24. The apparatus of claim 1, wherein the reticulated matrix comprises a polyurethane.

* * * * *